United States Patent
Zhao et al.

(10) Patent No.: US 11,229,796 B2
(45) Date of Patent: Jan. 25, 2022

(54) DEVICE, SYSTEM AND METHOD WITH ADAPTIVE TIMING FOR TISSUE CONDUCTION COMMUNICATION TRANSMISSION

(71) Applicant: Medtronic, Inc., Minneapolis, MN (US)

(72) Inventors: Yanzhu Zhao, Blaine, MN (US); Yong K. Cho, Excelsior, MN (US); Michael D. Eggen, Chisago City, MN (US); Wei Gan, Cincinnati, OH (US); Kathryn Hilpisch, Cottage Grove, MN (US); Srikara V. Peelukhana, Maple Grove, MN (US); Darrell J. Swenson, Lino Lakes, MN (US); Joshua J. Blauer, White Bear Township, MN (US)

(73) Assignee: Medtronic Inc., Minneapolis, MN (US)

( * ) Notice: Subject to any disclaimer, the term of this patent is extended or adjusted under 35 U.S.C. 154(b) by 357 days.

(21) Appl. No.: 16/220,093

(22) Filed: Dec. 14, 2018

(65) Prior Publication Data
US 2019/0184181 A1    Jun. 20, 2019

Related U.S. Application Data

(60) Provisional application No. 62/599,181, filed on Dec. 15, 2017.

(51) Int. Cl.
*A61N 1/372*     (2006.01)
*A61N 1/39*      (2006.01)
(Continued)

(52) U.S. Cl.
CPC ....... *A61N 1/37217* (2013.01); *A61N 1/3621* (2013.01); *A61N 1/36135* (2013.01);
(Continued)

(58) Field of Classification Search
CPC ............ A61N 1/37217; A61N 1/37276; A61N 1/37288; A61N 1/39622; A61N 1/36135;
(Continued)

(56) References Cited

U.S. PATENT DOCUMENTS 4,987,897 A    1/1991   Funke
5,591,214 A    1/1997   Lu
(Continued)

FOREIGN PATENT DOCUMENTS

WO    2016118845 A1    7/2016

OTHER PUBLICATIONS

Peichel et al., "Device and Method to Reduce Artifact From Tissue", U.S. Appl. No. 16/203,939, filed Nov. 29, 2018, 79 pages.
(Continued)

*Primary Examiner* — Eugene T Wu

(57) ABSTRACT

A device and method are described for transmitting tissue conductance communication (TCC) signals. A device may be is configured to establish a transmission window by transmitting a TCC test signal at multiple time points over a transmission test period to a receiving device and detect at least one response to the transmitted TCC test signals performed by the receiving device. The IMD is configured to establish the transmission window based on the at least one detected response so that the transmission window is correlated to a time of relative increased transimpedance between a transmitting electrode vector and receiving electrode vector during the transmission test period.

27 Claims, 9 Drawing Sheets

(51) Int. Cl.
*A61N 1/36* (2006.01)
*A61N 1/362* (2006.01)

(52) U.S. Cl.
CPC ..... *A61N 1/37252* (2013.01); *A61N 1/37276* (2013.01); *A61N 1/37288* (2013.01); *A61N 1/39622* (2017.08); *A61N 1/36031* (2017.08)

(58) Field of Classification Search
CPC .............. A61N 1/3621; A61N 1/37252; A61N 1/36031
See application file for complete search history.

(56) References Cited

U.S. PATENT DOCUMENTS

| | | | |
|---|---|---|---|
| 6,076,016 | A | 6/2000 | Feierbach |
| 6,115,636 | A | 9/2000 | Ryan |
| 7,542,800 | B2 | 6/2009 | Libbus et al. |
| 7,623,930 | B2 | 11/2009 | Zeijlemaker et al. |
| 7,912,537 | B2 | 3/2011 | Lee et al. |
| 8,041,418 | B2 | 10/2011 | Giftakis et al. |
| 8,055,345 | B2 | 11/2011 | Li et al. |
| 8,275,444 | B2 | 9/2012 | Zeijlemaker et al. |
| 8,412,352 | B2 | 4/2013 | Griswold et al. |
| 8,457,742 | B2 | 6/2013 | Jacobson |
| 8,720,276 | B2 | 5/2014 | Kuhn et al. |
| 8,738,126 | B2 | 5/2014 | Craig |
| 8,744,572 | B1 | 6/2014 | Greenhut et al. |
| 8,954,008 | B2 | 2/2015 | Wang et al. |
| 8,996,115 | B2 | 3/2015 | Trier et al. |
| 9,168,383 | B2 | 10/2015 | Jacobson et al. |
| 9,636,511 | B2 | 5/2017 | Carney et al. |
| 9,687,659 | B2 | 6/2017 | Von Arx et al. |
| 9,713,434 | B2 | 7/2017 | Barak |
| 2004/0011366 | A1 | 1/2004 | Schulman et al. |
| 2012/0109258 | A1 | 5/2012 | Cinbis et al. |
| 2012/0277600 | A1 | 11/2012 | Greenhut |
| 2012/0323099 | A1 | 12/2012 | Mothilal et al. |
| 2013/0253345 | A1 | 9/2013 | Griswold et al. |
| 2013/0324825 | A1 | 12/2013 | Ostroff et al. |
| 2014/0277286 | A1 | 9/2014 | Cinbis |
| 2015/0057721 | A1 | 2/2015 | Stahmann et al. |
| 2015/0306375 | A1 | 10/2015 | Marshall et al. |
| 2015/0306410 | A1 | 10/2015 | Marshall et al. |
| 2016/0144190 | A1 | 5/2016 | Cao et al. |
| 2016/0213937 | A1 | 7/2016 | Reinke et al. |
| 2016/0296760 | A1 | 10/2016 | Sahabi et al. |
| 2017/0173346 | A1 | 6/2017 | Kane et al. |
| 2017/0312531 | A1 | 11/2017 | Sawchuk |
| 2018/0207429 | A1* | 7/2018 | Reinke ................. A61B 5/0028 |
| 2019/0160290 | A1* | 5/2019 | Roberts .............. A61N 1/37217 |
| 2019/0160291 | A1* | 5/2019 | Peichel ................ A61N 1/3975 |
| 2019/0160292 | A1* | 5/2019 | Peichel .............. A61N 1/37217 |
| 2019/0160293 | A1* | 5/2019 | Reinke ................. A61N 1/3962 |

OTHER PUBLICATIONS

Reinke et al., "Tissue Conduction Communication Between Devices", U.S. Appl. No. 16/204,505, filed Nov. 29, 2018, 88 pages.
Roberts et al., "Signal Transmission Optimization for Tissue Conduction Communication", U.S. Appl. No. 16/202,418, filed Nov. 28, 2018, 82 pages.
Peichel, et al., "Tissue Conduction Communication using Ramped Drive Signal", U.S. Appl. No. 16/204,172, filed Nov. 29, 2016, 92 pages.
(PCT/US2018/065610) PCT Notification of Transmittal of the International Search Report and the Written Opinion of the International Searching Authority, dated Apr. 8, 2019, 10 pages.

* cited by examiner

DEVICE, SYSTEM AND METHOD WITH ADAPTIVE TIMING FOR TISSUE CONDUCTION COMMUNICATION TRANSMISSION

CROSS REFERENCE TO RELATED APPLICATIONS

This application claims the benefit of the filing date of provisional U.S. Patent Application No. 62/599,181, filed Dec. 15, 2017, the content of which is incorporated herein by reference in its entirety.

TECHNICAL FIELD

The disclosure relates generally to devices, systems and methods for communicating using tissue conduction communication.

BACKGROUND

Communication between two or more devices associated with a person, e.g., implanted within the person and/or attached to or otherwise contacting the person, may be desirable in a number of applications, such as for monitoring or managing health of a patient. Communication between these devices may, for example, enable the exchange of information, coordinated monitoring of a health condition and/or coordinated therapy to treat health conditions. Such systems, some examples of which are described below, may communicate using tissue conduction communication (TCC). TCC uses the human body as the medium of communication. TCC may sometimes be referred to as human body conduction (HBC) or intrabody communication.

A wide variety of implantable medical devices (IMDs) for delivering a therapy to or monitoring a physiological condition of a patient have been used clinically or proposed for clinical use in patients. Examples include IMDs that deliver therapy to and/or monitor conditions associated with the heart, muscle, nerve, brain, stomach or other tissue. Some therapies include the delivery of electrical stimulation to such tissues. Some IMDs may employ electrodes for the delivery of therapeutic electrical signals to such organs or tissues, electrodes for sensing intrinsic physiological electrical signals within the patient, which may be propagated by such organs or tissue, and/or other sensors for sensing physiological signals of a patient.

Implantable cardioverter defibrillators (ICDs), for example, may be used to deliver high energy defibrillation and/or cardioversion shocks to a patient's heart when atrial or ventricular tachyarrhythmia, e.g., tachycardia or fibrillation, is detected. An ICD may detect a tachyarrhythmia based on an analysis of a cardiac electrogram sensed via electrodes, and may deliver anti-tachyarrhythmia shocks, e.g., defibrillation shocks and/or cardioversion shocks, via electrodes. An ICD or an implantable cardiac pacemaker, as another example, may provide cardiac pacing therapy to the heart when the natural pacemaker and/or conduction system of the heart fails to provide synchronized atrial and ventricular contractions at rates and intervals sufficient to sustain healthy patient function. ICDs and cardiac pacemakers may also provide overdrive cardiac pacing, referred to as anti-tachycardia pacing (ATP), to suppress or convert detected tachyarrhythmias in an effort to avoid cardioversion/defibrillation shocks.

Some IMDs are coupled to one or more of the electrodes used to sense electrical physiological signals and deliver electrical stimulation via one or more leads. A medical electrical lead carrying sensing and/or electrical therapy delivery electrodes allow the IMD housing to be positioned a location spaced apart from the target site for sensing and/or stimulation delivery. For example, a subcutaneously or sub-muscularly implanted housing of an ICD or implantable cardiac pacemaker may be coupled to endocardial electrodes via one or more medical electrical leads that extend transvenously to the patient's heart. Other ICD systems, referred to as extracardiovascular ICD systems, are not coupled to any transvenous leads, and instead sense and deliver shocks via electrodes implanted away from the patient's heart, e.g., implanted subcutaneously or substernally. The extra-cardiovascular electrodes may be provided along the housing of the subcutaneous ICD and/or coupled to the housing via one or more leads extending subcutaneously, submuscularly or substernally from the housing.

Leadless IMDs may also be used to deliver therapy to a patient, and/or sense physiological parameters of a patient. In some examples, a leadless IMD may include one or more electrodes on its outer housing to deliver therapeutic electrical stimulation to patient, and/or sense intrinsic electrical signals of patient. For example, a leadless pacemaker may be used to sense intrinsic depolarizations or other physiological parameters of the patient, and/or deliver therapeutic electrical stimulation to the heart. A leadless pacemaker may be positioned within or outside of the heart and, in some examples, may be anchored to a wall of the heart via a fixation mechanism.

In some situations, two or more IMDs are implanted within a single patient. It may be desirable for the two or more IMDs to be able to communicate with each other, e.g., to coordinate, or cooperatively provide, sensing for monitoring the patient and/or therapy delivery. Although some IMDs communicate with other medical devices, e.g., with external programming devices, using radio-frequency (RF) telemetry, TCC allows for communication between two or more IMDs by transmitting signals between the electrodes of two IMDs via a conductive tissue pathway. Likewise, TCC may be utilized to communicate between an IMD and an external device having electrodes proximate to or in contact with the skin of the patient or between two external devices having electrodes proximate to or in contact with the skin of the patient.

SUMMARY

The techniques of this disclosure generally relate to TCC signal transmission techniques performed by a device. The techniques of this disclosure are described in the context of an IMD. However, the techniques can be utilized by any device, medical or non-medical, implanted or external, that communicates using TCC. An IMD operating according to the techniques disclosed herein transmits test TCC signals at multiple times over a transmission test period and detects at least one response to the test TCC signals. The response is performed by a receiving device configured to receive the test TCC signals. The IMD may establish a TCC transmission window as a time window that is directly correlated to a time of increased or maximized transimpedance between a transmitting electrode vector of the transmitting IMD and a receiving electrode vector of the receiving device. The transmitting IMD transmits communication signals by a TCC transmitter during the TCC transmission window to promote reliable communication between the transmitting IMD and the receiving device for coordinating patient monitoring and/or automatic therapy delivery.

In one example, the disclosure provides a device comprising a housing and a TCC transmitter and a control circuit enclosed by the housing. The TCC transmitter is configured to generate TCC signals for transmission via a transmitting electrode vector coupled to the TCC transmitter. The control circuit is configured to control the TCC transmitter to transmit a TCC test signal at multiple time points over a transmission test period and detect at least one response to the transmitted TCC test signals performed by the receiving device. The control circuit is configured to establish a transmission window based on the at least one response so that the transmission window is correlated to a time of relative increased transimpedance between the transmitting electrode vector and a receiving electrode vector of the receiving device during the transmission test period. The control circuit may be configured to control the TCC transmitter to transmit a communication signal to the receiving device during the transmission window.

In another example, the disclosure provides a method that includes transmitting a TCC test signal at each of a plurality of time points over a transmission test period via a transmitting electrode vector coupled to the TCC transmitter and detecting at least one response to the transmitted TCC test signals performed by a receiving device. The method further includes establishing a transmission window based on the at least one response so that the transmission window is correlated to a time of relative increased transimpedance between the transmitting electrode vector and a receiving electrode vector of the receiving device during the transmission test period and transmitting a TCC signal to the receiving device during the transmission window.

In another example, the disclosure provides a non-transitory, computer-readable storage medium storing a set of instructions which, when executed by a device, cause the device to transmit a TCC test signal at multiple time points over a transmission test period to a receiving device via a transmitting electrode vector coupled to the TCC transmitter and a conductive tissue pathway in a patient. The IMD is further caused to detect at least one response to the transmitted TCC test signals performed by the receiving device and establish a transmission window based on the at least one response. The established transmission window is correlated to a time during the transmission test period of relative increased transimpedance between the transmitting electrode vector and a receiving electrode vector of the receiving device. The IMD is further caused to transmit a TCC signal to the receiving device during the transmission window.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
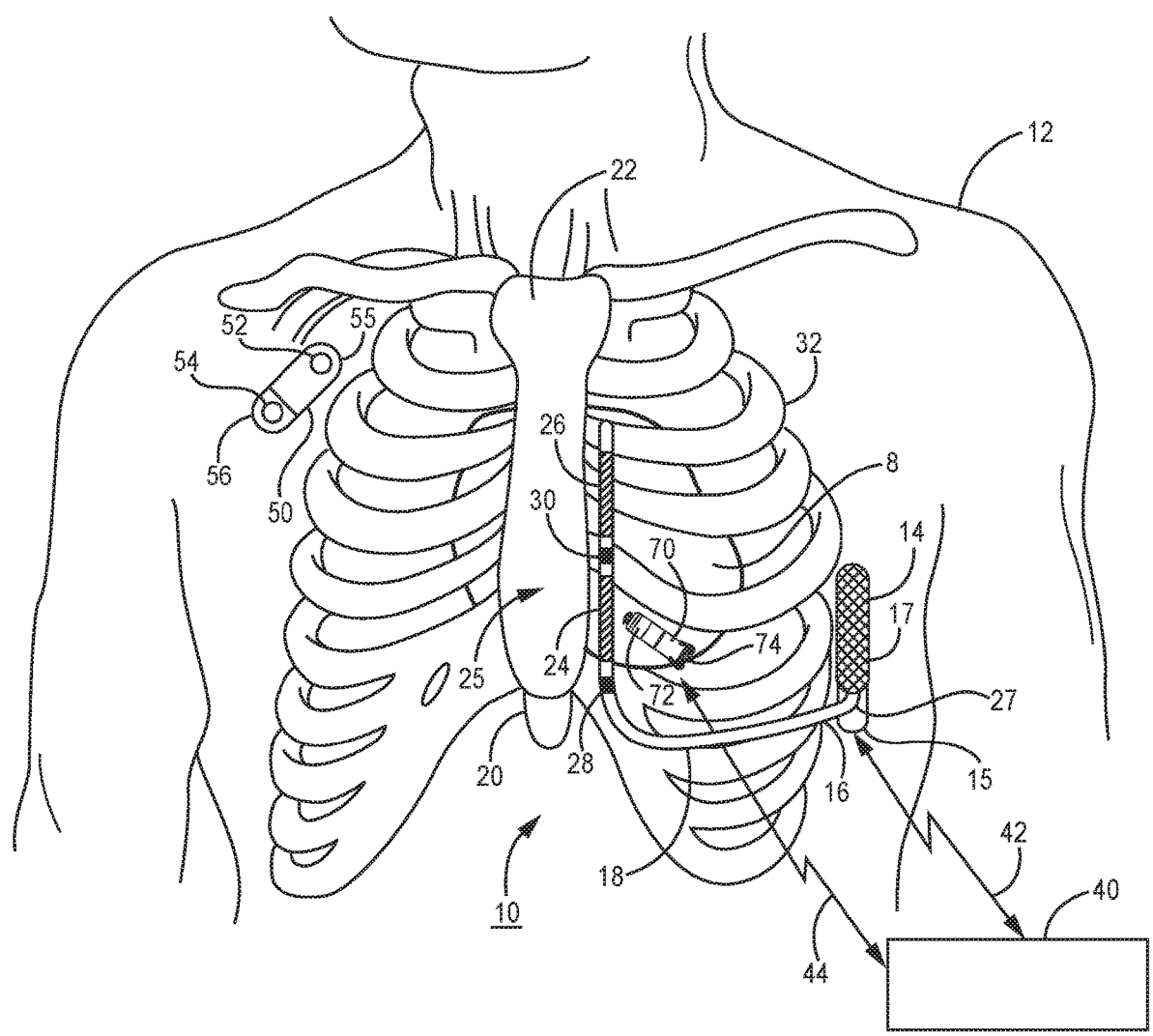
FIG. 1 is a conceptual diagram of an IMD system capable of TCC according to one example.

Wireless communication between two or more medical devices may be desired for a number of reasons, including to exchange data and/or to coordinate, or cooperatively provide, sensing of physiological signals and/or therapy delivery. TCC signals may be wirelessly transmitted from one IMD to one or more IMDs co-implanted within a patient and/or to an external medical device having skin or surface electrodes coupled to the patient for transmitting and/or receiving TCC signals. As used herein, the term "wireless" refers to a lack of a wire or other physical electrical connection or conductor that carries a communication signal from one medical device having communication circuitry enclosed by one housing to another medical device having communication circuitry enclosed by another housing that is physically spaced apart from the first housing.

TCC signals may be transmitted wirelessly by injecting a current signal into an electrically conductive body tissue pathway via a transmitting electrode vector. The current spreads through the patient's body, e.g., through the thorax, abdomen, muscle tissue, blood volumes or other body regions, producing an electrical potential field. The receiving device may detect the transmitted TCC signal by measuring the potential difference between two of its electrodes selected as a receiving electrode vector. Optimally, the receiving electrode vector is parallel to the tissue conduction pathway of the injected current to maximize the potential difference developed on the receiving electrode pair. If the receiving electrode vector is orthogonal to the pathway of the current flow through the body tissue, a null signal may result.

The current injected to transmit the TCC signal is of sufficient amplitude to produce a voltage potential that can be detected by an intended receiving device but should at the same time not capture excitable body tissue, e.g., causing unintended stimulation of nerve or muscle tissue, possibly leading to muscle contraction, pain or even cardiac capture. The voltage signal strength developed across the receiving electrode vector depends at least in part on the transimpedance of the TCC transmission pathway. The transimpedance is the voltage received at a receiving electrode vector divided by the transmitted current (voltage out divided by current in). By increasing or maximizing transimpedance, the voltage signal at the intended receiving electrodes is maximized for a given current signal injected into the conductive tissue pathway. In this way, reliable wireless communication may be achieved using a minimized current signal amplitude of the transmitted TCC signal to avoid unintended stimulation of body tissue by the TCC signal, conserve battery charge of the transmitting device, and reduce the likelihood of interference of the TCC signal with other sensing electrodes in the IMD system.

The transmitting electrode vector and/or the receiving electrode vector may be subjected to patient body motion such that the relative alignment of the transmitting and receiving electrode vectors varies over time. As such, the transimpedance for a given TCC communication electrode vector may vary with patient body motion. Cardiac motion, respiratory motion, musculoskeletal movement or other motion of the body tissue may cause relative changes in the alignment of the transmitting and receiving electrode vectors, depending on the implanted and/or external location of transmitting and receiving electrode vectors. The techniques disclosed herein provide adaptive timing of TCC signal transmission to increase the likelihood that a TCC signal is transmitted at a time when transimpedance is relatively high and thereby promote a high received signal strength and high probability of successful TCC signal reception.

FIG. 1 is a conceptual diagram of an IMD system 10 capable of TCC according to one example. FIG. 1 is a front view of a patient 12 implanted with an ICD 14, an extra-cardiovascular electrical stimulation and sensing lead 16 coupled to ICD 14, an intracardiac pacemaker 70, and a wireless sensor 50. In some examples, ICD 14 and/or sensor 50 may be configured to communicate with pacemaker 70 via TCC for transmitting a variety of data or commands. For example, ICD 14 or sensor 50 may be configured to communicate with a leadless intracardiac pacemaker 70 via TCC to confirm detected cardiac events or a detected heart rhythm and/or coordinate delivery of cardiac pacing pulses for bradycardia pacing, ATP therapy, post-shock pacing, cardiac resynchronization therapy (CRT) or other electrical stimulation therapies in response to an abnormal heart rhythm being detected by ICD 14 or sensor 50. It is recognized that in some examples, only sensor 50 or only ICD 14 is present in patient 12 for communicating with pacemaker 70. Moreover, the techniques described herein may be utilized by two external devices that communicate using TCC or between one of implanted devices 10, 50 or 70 and an external device 40. The techniques may also have non-medical applications as well for devices that are implanted and/or external and communicate using TCC.

IMD system 10 senses cardiac electrical signals, such as R-waves attendant to ventricular depolarizations and/or P-waves attendant to atrial depolarizations, for detecting abnormal heart rhythms with high sensitivity and specificity to enable IMD system 10 to deliver (or withhold) appropriate therapies at appropriate times. In one example, pacemaker 70 may be a triggered pacemaker that is triggered to deliver a cardiac pacing pulse in response to receiving a transmitted TCC signal from ICD 14 or sensor 50. For instance, pacemaker 70 may be implanted in the right or left ventricle of the patient's heart 8 for delivering atrial synchronized ventricular pacing. ICD 14 or sensor 50 may be configured to sense atrial P-waves and transmit a TCC signal to pacemaker 70 at an appropriate time following a sensed P-wave. In response to detecting the TCC signal, pacemaker 70 may deliver a ventricular pacing pulse without delay or at a programmed AV pacing interval after receiving the TCC signal.

In various examples, ICD 14 may operate as a control device and transmit data or commands to sensor 50 or to pacemaker 70 configured to operate as responders. Data or commands transmitted by ICD 14 may include programmable operating parameters used by sensor 50 in sensing physiological signals or by pacemaker 70 in delivering cardiac electrical stimulation pulses. In some examples, TCC signals transmitted by ICD 14 may include commands to acquire data, transmit data back to ICD 14, or deliver therapy (in the case of pacemaker 70).

In other examples, sensor 50 may be configured to operate as a control device transmitting TCC signals to pacemaker 70 configured to operate as a responder. Sensor 50 may sense cardiac electrical signals and transmit a pacing trigger signal to pacemaker 70 as a TCC signal to command pacemaker 70 to deliver a pacing pulse at an appropriate pacing interval following a cardiac event, e.g., a P-wave, sensed by sensor 50.

FIG. 1 is described in the context of an IMD system 10 including ICD 14, pacemaker 70 and/or sensor 50 capable of sensing cardiac electrical signals produced by the patient's heart 8 and delivering cardioversion and/or defibrillation (CV/DF) shocks and cardiac pacing pulses to the patient's heart 8. It is recognized, however, that aspects of the TCC signal transmission techniques disclosed herein may be implemented in a variety of IMD systems which may include an ICD, pacemaker, cardiac monitor or other sensing-only device, neurostimulator, drug delivery device or other implantable medical device(s). The TCC signal transmission techniques disclosed herein may be implemented in any IMD system that requires communication between one IMD and at least one other medical device, implanted or external, and wherein at least one of the devices communicating via TCC is subjected to the movement of the heart, lungs, musculoskeletal system, or other patient body motion including postural changes that may alter the alignment of the TCC transmitting and receiving electrode vectors.

The techniques disclosed herein provide adaptive timing of TCC signal transmission to account for changes in the relative alignment of the transmitting and receiving electrode vectors that results in changes in the transimpedance between the transmitting and receiving electrode vectors. A low transimpedance, e.g. due to the receiving electrode vector becoming relatively more orthogonal to the conductive tissue pathway of an injected TCC current signal, may reduce the voltage signal developed at the receiving electrode pair, potentially resulting in failed communication.

ICD 14 includes a housing 15 that forms a hermetic seal that protects internal components of ICD 14. The housing 15 of ICD 14, as well as the housings of sensor 50 and pacemaker 70, may be formed of a conductive material, such as titanium or titanium alloy. The ICD housing 15 may function as an electrode (sometimes referred to as a "can" electrode). In other instances, the housing 15 of ICD 14 may include a plurality of electrodes on an outer portion of the housing. The outer portion(s) of the housing 15 functioning as an electrode(s) may be coated with a material, such as titanium nitride for reducing post-stimulation polarization artifact. Housing 15 may be used as an active can electrode for use in delivering CV/DF shocks or other high voltage pulses delivered using a high voltage therapy circuit. In other examples, housing 15 may be available for use in delivering relatively lower voltage cardiac pacing pulses and/or for sensing cardiac electrical signals in combination with electrodes carried by lead 16. In any of these examples, housing 15 may be used in a transmitting and receiving electrode vector for transmitting TCC signals according to the techniques disclosed herein.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. Housing 15 may house one or more processors, memories, transceivers, cardiac electrical signal sensing circuitry, therapy delivery circuitry, TCC transmitting and receiving circuitry, power sources and other components for sensing cardiac electrical signals, detecting a heart rhythm, and controlling and delivering electrical stimulation pulses to treat an abnormal heart rhythm and for transmitting TCC signals to pacemaker 70 and/or receiving TCC signals from pacemaker 70. ICD 14 may correspond to an ICD configured to transmit TCC signals as generally disclosed in U.S. patent application Ser. No. 16/204,505 (Carney, et al.), incorporated herein by reference in its entirety.

Lead 16 includes an elongated lead body 18 having a proximal end 27 that includes a lead connector (not shown) configured to be connected to ICD connector assembly 17 and a distal portion 25 that includes one or more electrodes. In the example illustrated in FIG. 1, the distal portion 25 of lead body 18 includes defibrillation electrodes 24 and 26 and pace/sense electrodes 28 and 30. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be selectively activated independently.

Electrodes 24 and 26 (and in some examples housing 15) are referred to herein as defibrillation electrodes because they are utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to pacing and sensing electrodes 28 and 30. However, electrodes 24 and 26 and housing 15 may also be utilized to provide pacing functionality, sensing functionality, and/or TCC signal transmission and receiving in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. For example, electrodes 24 and 26 may be used in a sensing electrode vector used to sense cardiac electrical signals and detect and discriminate tachyarrhythmias.

Electrodes 24 and 26 may be used in a TCC signal transmission vector in combination with each other, collectively with housing 15, or individually with housing 15. In the case of ICD 14 being configured to receive TCC signals from pacemaker 70, electrodes 24, 26 and/or housing 15 may be used in a TCC receiving electrode vector. The transmitting and receiving electrode vectors may be the same or different vectors. The low impedance of the high surface area defibrillation electrodes 24 and 26 and housing 15 is advantageous in TCC signal transmission since a low impedance of the transmitting electrode vector is positively correlated to the strength of the injected current signal for a given drive signal produced by a TCC transmitter included in ICD 14.

Electrodes 28 and 30 are relatively smaller surface area electrodes which are available for use in sensing electrode vectors for sensing cardiac electrical signals and may be used for delivering relatively low voltage pacing pulses in some configurations. Electrodes 28 and 30 are referred to as pace/sense electrodes because they are generally configured for use in low voltage applications, e.g., delivery of relatively low voltage pacing pulses and/or sensing of cardiac electrical signals, as opposed to delivering high voltage cardioversion defibrillation shocks. In some instances, electrodes 28 and 30 may provide only pacing functionality, only sensing functionality or both. Furthermore, one or both of electrodes 28 and 30 may be used in TCC signal transmission and/or receiving in some examples.

ICD 14 may obtain cardiac electrical signals corresponding to electrical activity of heart 8 via a combination of sensing electrode vectors that include combinations of electrodes 24, 26, 28, 30 and/or housing 15. Various sensing electrode vectors utilizing combinations of electrodes 24, 26, 28, and 30 may be selected by sensing circuitry included in ICD 14 for receiving a cardiac electrical signal via one or more sensing electrode vectors. Electrodes 28 and 30 may be ring electrodes, short coil electrodes, hemispherical electrodes, or the like and may be positioned at other locations along lead body 18. Electrodes 24, 26, 28 and 30 are not limited to the positions and arrangement shown in FIG. 1. Furthermore, lead 16 may include fewer or more electrodes than shown in FIG. 1.

The TCC transmitting electrode vector may be selected to reduce impedance of the transmitting electrode vector and increase transimpedance from the transmitting electrode vector to the intended receiving electrode vector. Among the factors that may contribute to an increased transimpedance of the TCC pathway, and therefore maximized strength of the receive voltage signal, are a substantially parallel electrical configuration of the receiving electrode vector to the conductive tissue pathway, relatively wide spacing of the transmitting electrodes, relatively wide spacing of the receiving electrodes, and close proximity of the transmitting electrode vector to the receiving electrode vector.

A parallel electrical configuration between the transmitting and receiving electrode vectors for maximizing the received signal may coincide with physically parallel electrode pairs. The physical electrode vectors may be viewed in some cases as the line the extends from one electrode of the vector to the other electrode of the vector to determine orientation of the transmitting and received vectors relative to one another. In some instances, however, physically parallel electrode pairs may not be electrically parallel depending on the electrical conduction properties of the intervening tissues. For example, a body tissue having relatively low electrical conductance, such as lung tissue, compared to other surrounding tissues, may require a physical electrode configuration that is not necessarily parallel in order to achieve an electrical configuration that aligns the receiving electrode vector substantially parallel to the direction of the current flow along the conductive tissue pathway.

In one example, defibrillation electrode 24 may be selected in combination with housing 15 for transmitting TCC signals to pacemaker 70. In other examples, TCC signals may be transmitted by ICD 14 using defibrillation electrode 26 and housing 15 or using two defibrillation electrodes 24 and 26. The transmitting electrode vector impedance (delivered voltage divided by delivered current) may be up to hundreds of ohms. The transimpedance of the TCC pathway that includes a transmitting electrode vector including one defibrillation electrode 24 or 26 paired with housing 15 may be less than 10 ohms and even less than 1 ohm. A high transimpedance at the TCC signal transmission frequency is desired to produce a relatively high voltage on the receiving electrodes for a given injected current of the TCC signal.

The electrode pair selected for transmitting TCC signals may include one or both of pace/sense electrodes 28 and 30 in some examples. For example, the pace/sense electrode 28 or 30 may be paired with housing 15, defibrillation electrode 24 or defibrillation electrode 26 for transmitting TCC signals. The impedance of the transmitting electrode vector may be increased due to the relatively smaller surface area of pace/sense electrodes 28 and 30, which may have the effect of lowering the injected current during TCC signal transmission and thereby lowering the received voltage signal at the receiving electrode vector, but a tradeoff in achieving a higher transimpedance may exist. ICD 14 may be configured to select a TCC transmitting electrode vector from among multiple possible vectors using electrodes 24, 26, 28, 30 and housing 15 to achieve the best TCC signal strength at the receiving electrodes of pacemaker 70.

In the example shown, lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superior subcutaneously or submuscularly over the ribcage and/or sternum or substernally under the ribcage and/or sternum 22. Although illustrated in FIG. 1 as being offset laterally from and extending substantially parallel to sternum 22, the distal portion 25 of lead 16 may be implanted at other locations, such as over sternum 22, offset to the right or left of sternum 22, angled laterally from sternum 22 toward the left or the right, or the like. Alternatively, lead 16 may be placed along other subcutaneous, submuscular or substernal paths. The path of extra-cardiovascular lead 16 may depend on the location of ICD 14, the arrangement and position of electrodes carried by the lead body 18, and/or other factors.

Electrical conductors (not illustrated) extend through one or more lumens of the elongated lead body 18 of lead 16 from the lead connector at the proximal lead end 27 to electrodes 24, 26, 28, and 30 located along the distal portion 25 of the lead body 18. The elongated electrical conductors contained within the lead body 18 are each electrically coupled with respective defibrillation electrodes 24 and 26 and pace/sense electrodes 28 and 30, which may be separate respective insulated conductors within the lead body 18. The respective conductors electrically couple the electrodes 24, 26, 28, and 30 to circuitry of ICD 14, such as a signal generator for therapy delivery and TCC signal transmission and/or a sensing circuit for sensing cardiac electrical signals and/or receiving TCC signals, via connections in the connector assembly 17, including associated electrical feedthroughs crossing housing 15.

The electrical conductors transmit therapy from a therapy delivery circuit within ICD 14 to one or more of defibrillation electrodes 24 and 26 and/or pace/sense electrodes 28 and 30 and transmit sensed electrical signals from one or more of defibrillation electrodes 24 and 26 and/or pace/sense electrodes 28 and 30 to the sensing circuit within ICD 14. The electrical conductors also transmit TCC signals from a TCC transmitter to electrodes selected for transmitting the TCC signals. In some examples, ICD 14 may receive TCC signals from pacemaker 70 in which case the TCC signals are conducted from a receiving pair of electrodes to a TCC signal detector enclosed by housing 15.

The lead body 18 of lead 16 may be formed from a non-conductive material and shaped to form one or more lumens within which the one or more conductors extend. Lead body 18 may be a flexible lead body that conforms to an implant pathway. In other examples, lead body 18 may include one or more preformed curves. Various example configurations of extra-cardiovascular leads and electrodes and dimensions that may be implemented in conjunction with the TCC transmission techniques disclosed herein are described in pending U.S. Publication No. 2015/0306375 (Marshall, et al.) and pending U.S. Publication No. 2015/0306410 (Marshall, et al.), both of which are incorporated herein by reference in their entirety.

ICD 14 analyzes the cardiac electrical signals received from one or more sensing electrode vectors to monitor for abnormal rhythms, such as bradycardia, tachycardia or fibrillation. ICD 14 may analyze the heart rate and morphology of the cardiac electrical signals to monitor for tachyarrhythmia in accordance with any of a number of tachyarrhythmia detection techniques. ICD 14 generates and delivers electrical stimulation therapy in response to detecting a tachyarrhythmia, e.g., ventricular tachycardia (VT) or ventricular fibrillation (VF), using a therapy delivery electrode vector which may be selected from any of the available electrodes 24, 26, 28 30 and/or housing 15. ICD 14 may deliver ATP in response to VT detection, and in some cases may deliver ATP prior to a CV/DF shock or during high voltage capacitor charging in an attempt to avert the need for delivering a CV/DF shock. If ATP does not successfully terminate VT or when VF is detected, ICD 14 may deliver one or more CV/DF shocks via one or both of defibrillation electrodes 24 and 26 and/or housing 15. ICD 14 may generate and deliver other types of electrical stimulation pulses such as post-shock pacing pulses or bradycardia pacing pulses using a pacing electrode vector that includes one or more of the electrodes 24, 26, 28, and 30 and the housing 15 of ICD 14.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferiorly from the manubrium to the desired location subcutaneously or submuscularly. In yet another example, ICD 14 may be placed abdominally.

Sensor 50 may be a cardiac electrical signal sensor that is implanted subcutaneously, submuscularly or within ribcage 32 for sensing depolarizations of the heart 8, e.g., P-waves attendant to atrial depolarizations and R-waves attendant to ventricular depolarizations. A cardiac electrical signal produced by heart 8 may be received by housing-based electrodes 52 and 54 coupled to sensing circuitry enclosed by the housing 55 of sensor 50. Housing 55 may be formed from a conductive metal, e.g., titanium or titanium alloy. Exterior portions of housing 55 not functioning as an electrode may be covered by an electrically insulating coating, leaving an uninsulated portion exposed to function as electrode 52. Electrode 54 may be carried by a header 56, formed of an electrically insulative polymer, and coupled to a sensing circuit enclosed by housing 50 via an electrical feedthrough extending from header 56 across housing 50. Header 56 is hermetically sealed to housing 50 to protect internal circuitry.

Internal circuitry may include a processor or controller for controlling sensor functions and a sensing circuit for receiving a cardiac electrical signal and generating an electrocardiogram (ECG) signal that may be stored and transmitted to external device 40. The sensing circuit may include filters, amplifiers, an analog-to-digital converter, rectifier and comparator, sense amplifier or other cardia event detector for detecting cardiac events, such as P-waves and R-waves. Sensor 50 may include a TCC transmitter and a TCC signal detector configured to enable TCC communication between sensor 50 and pacemaker 70 and/or ICD 14. In one example, sensor 50 detects P-waves from a cardiac electrical signal and the sensor controller may control the TCC transmitter to transmit TCC signals to pacemaker 70 to trigger ventricular pacing pulse delivery by pacemaker 70 at a desired atrioventricular (AV) time interval following the sensed P-wave. In this way, the sensor 50 and pacemaker 70 cooperatively provide atrial-synchronized ventricular pacing. The internal circuitry of sensor 50 may further include an RF transceiver for communicating with external device 40 (and/or ICD 14).

While sensor 50 is described primarily as a cardiac electrical signal sensor, it is recognized that sensor 50 may include other sensors, e.g., an optical sensor for monitoring tissue perfusion, or monitor other electrical signals or events, e.g., impedance signals for detecting physiological conditions or events. Sensor 50 may acquire and/or transmit physiological signal data to ICD 14 upon demand via TCC signal transmission. As such, sensor 50 may be configured to operate as a control device with pacemaker 70 functioning as a responder for delivering triggered cardiac pacing pulses to heart 8. Sensor 50 may additionally or alternatively be configured to operate as a responder with ICD 14 functioning as a control device transmitting commands or requests to sensor 50.

Pacemaker 70 is shown as a leadless intracardiac pacemaker configured to receive TCC signals from ICD 14 and/or sensor 50 via housing-based electrodes 72 and 74 and may be configured to transmit TCC signals via housing-based electrodes 72 and 74 to ICD 14 and/or sensor 50. Pacemaker 70 may be delivered transvenously and anchored by a fixation member at an intracardiac pacing and sensing site. For example, pacemaker 70 may be implanted in an atrial or ventricular chamber of the patient's heart. In further examples, pacemaker 70 may be attached to an external surface of heart 8 (e.g., in contact with the epicardium) such that pacemaker 70 is disposed outside of heart 8.

Pacemaker 70 is configured to deliver cardiac pacing pulses via a pair of housing-based electrodes 72 and 74 and may be configured to sense cardiac electrical signals for determining the need for a delivered pacing pulse. For example, pacemaker 70 may deliver bradycardia pacing pulses, rate responsive pacing pulses, ATP, post-shock pacing pulses, CRT, and/or other pacing therapies. Pacemaker 70 may include a TCC signal detector (which may also be referred to as a "TCC signal receiver") that receives and demodulates TCC signals transmitted from ICD 14 and/or sensor 50 via housing-based electrodes 72 and 74. Pacemaker 70 may include a TCC transmitter that transmits TCC signals to ICD 14 and/or sensor 50 via the housing-based electrodes 72 and 74. Pacemaker 70 may include circuitry and components as described in greater detail below in conjunction with FIGS. 3 and 4. An example intracardiac pacemaker that may be included in an IMD system employing TCC is described in U.S. Pat. No. 8,744,572 (Greenhut et al.) incorporated herein by reference in its entirety. In other examples, TCC signal detector 175 and/or TCC transmitter 90 may be distinct components separate from sensing circuit 174 and signal generator 176, respectively. For example, ICD 14 may include a TCC transceiver that incorporates the circuitry of TCC signal detector 175 and/or TCC transmitter 90. In this case, the functionality described with respect to TCC signal detector 175 and/or TCC transmitter 90 may be performed via a distinct TCC component instead of being part of sensing circuit 174 and signal generator 176.

Pacemaker 70 may be implanted in or along the right atrium, the left atrium, the right ventricle or the left ventricle of heart 8 to sense electrical activity of heart 8 and deliver pacing therapy. ICD 14 and/or sensor 50 may be configured to transmit TCC signals to pacemaker 70 implanted within the patient's heart 8 to coordinate electrical stimulation therapy delivery. For example, ICD 14 or sensor 50 may transmit command signals to cause pacemaker 70 to deliver a triggered cardiac pacing pulse, start an ATP therapy, or request confirmation of sensed cardiac electrical events or a tachyarrhythmia detection. Pacemaker 70 may sense cardiac electrical signals using electrodes 152 and 160, but when pacemaker 70 is implanted in the right or left ventricle to provide ventricular pacing, relatively low amplitude P-waves produced by the atrial chambers may be difficult to detect by pacemaker 70. As such, sensor 50 or ICD 14 may be enabled to sense P-waves and control pacemaker 70 to deliver appropriately timed ventricular pacing pulses by transmitting a pacing trigger signal as a TCC signal for cooperatively providing atrial-synchronized ventricular pacing.

Pacemaker 70 implanted in or on the heart is subjected to continuous cardiac motion. As such, the alignment of a receiving electrode vector defined by electrodes 72 and 74 with a transmitting electrode vector of sensor 50, e.g., electrodes 52 and 54, or a transmitting electrode vector of ICD 14, e.g., defibrillation electrode 24 or 26 paired with housing 15, is continuously changing in a time-varying, cyclical manner corresponding to the cardiac cycle. Likewise, respiratory motion of the patient's lungs will cause time-varying cyclical changes in the alignment of pacemaker electrodes 72 and 74 used as a TCC receiving electrode vector relative to a transmitting electrode vector of sensor 50 and/or ICD 14. Both pacemaker 70, acting as a receiving device, and sensor 50 or ICD 14, acting as a transmitting device, may be subjected to respiratory motion when implanted in the locations shown in or around the ribcage 32. Furthermore, ICD 14, sensor 50 and pacemaker 70 may all be subjected to patient body motion due to physical activity and posture changes which may further impact the alignment of the TCC transmitting and receiving electrode vectors of IMD system 10. For example, postural changes from upright to non-upright positions or between supine, prone and side lying positions may alter the relative alignment between transmitting and receiving electrode vectors.

As such, numerous cyclical and/or non-cyclical changes in the relative alignment of the receiving electrode vector to the conductive tissue pathway of the injected TCC current signal may alter the transimpedance coupling the injected current signal to the receiving electrode vector. At times, the transimpedance may be increased, increasing the received signal strength, but at other times the transimpedance may be decreased, reducing the received signal strength and potentially resulting in failed communication. In the example of pacemaker 70 operating as a triggered pacemaker that responds to a TCC signal by scheduling and delivering a pacing pulse, a failed communication may result in asystole or a delayed pacing pulse delivered as a backup pacing pulse by pacemaker 70 in the absence of a received TCC trigger signal. Using the techniques disclosed herein, adaptive timing of the TCC signal transmission by the transmitting device promotes reliable TCC signal reception by the receiving device. The adaptive timing may include identifying time intervals that correspond to relatively higher transimpedance and selecting a TCC signal transmission time within the identified time intervals.

An external device 40 may be in telemetric communication with ICD 14 by a wireless communication link 42, pacemaker 70 via a wireless communication link 44 and sensor 50 (communication link to be understood but not shown for the sake of clarity of FIG. 1). External device 40 may include a processor, display, user interface, telemetry unit and other components for communicating with ICD 14, sensor 50 and pacemaker 70 for transmitting and receiving data via communication link 42 and 44, respectively. Communication link 42 or 44 may be established between ICD 14 or pacemaker 14, respectively, and external device 40 using a radio frequency (RF) link such as BLUETOOTH®, Wi-Fi, or Medical Implant Communication Service (MICS) or other RF or communication frequency bandwidth. In some examples, ICD 14, sensor 50, and pacemaker 70 may communicate with an external device 40 using TCC, e.g., using receiving surface electrodes coupled to external device 40 that are placed externally on patient 12.

External device 40 may be embodied as a programmer used in a hospital, clinic or physician's office to retrieve data from ICD 14 and to program operating parameters and algorithms in ICD 14 for controlling ICD functions. External device 40 may be used to program cardiac event sensing parameters (e.g., R-wave sensing parameters), cardiac rhythm detection parameters (e.g., VT and VF detection parameters) and therapy control parameters used by ICD 14. Data stored or acquired by ICD 14, including physiological signals or associated data derived therefrom, results of device diagnostics, and histories of detected rhythm episodes and delivered therapies, may be retrieved from ICD 14 by external device 40 following an interrogation command. External device 40 may alternatively be embodied as a home monitor or hand held device.

In some examples, pacemaker 70 is not capable of bidirectional communication with external device 40. ICD 14 or sensor 50 may operate as a control device and pacemaker 70 as a responder. Pacemaker 70 may receive TCC communication signals from ICD 14 or sensor 50 that include operating control data and commands (which may be transmitted from external device 40 to ICD 14 or sensor 50) so that RF telemetry circuitry need not be included in pacemaker 70. Pacemaker 70 may transmit data, such as information related to delivered pacing therapy and/or acquired cardiac electrical signals on command from ICD 14 or sensor 50 via TCC transmissions, and ICD 14 or sensor 50 may transmit data received from pacemaker 70 to external device 40 via RF communication.

Figure 2:
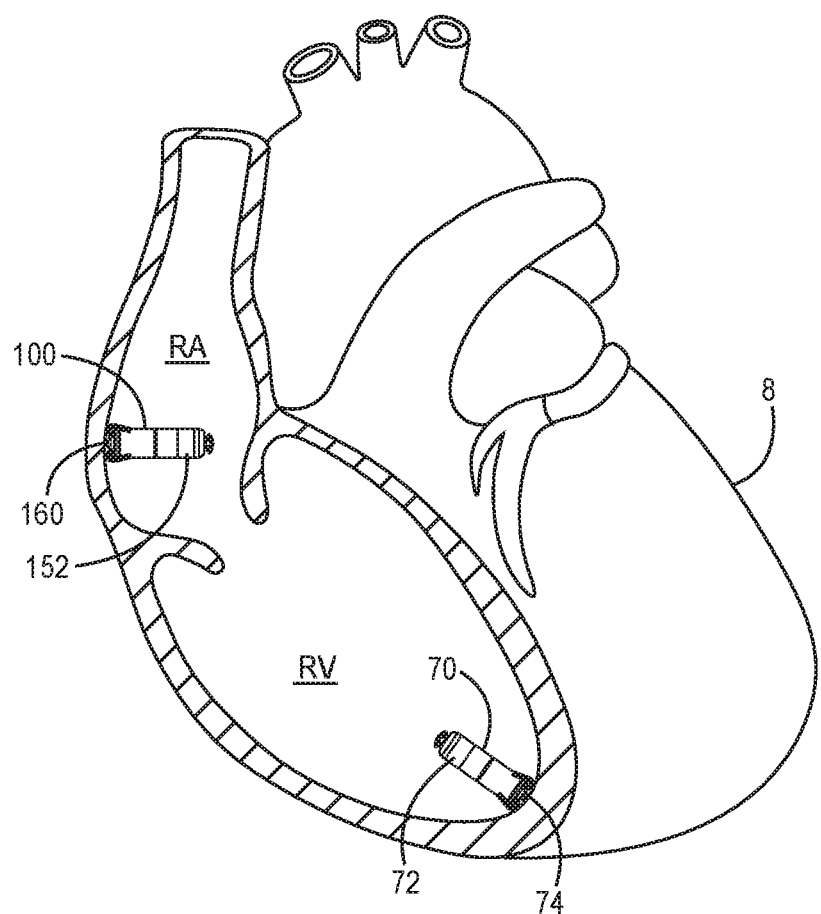
FIG. 2 is a conceptual diagram of an IMD system configured to communicate using TCC techniques disclosed herein according to another example.

FIG. 2 is a conceptual diagram of an IMD system 101 configured to communicate using TCC transmission techniques disclosed herein according to another example. The IMD system 101 may include two leadless, intracardiac pacemakers 100 and 70. Pacemaker 70 is shown implanted in the right ventricle (RV) of the patient's heart 8 and is referred to hereafter a RV pacemaker 70 and pacemaker 100 is shown implanted in the right atrium (RA) and is referred to hereafter as RA pacemaker 100. However, it is to be understood that pacemakers 100 and 70 may be implanted in or along other cardiac chambers and are not limited to being a RA pacemaker 100 and RV pacemaker 70 in an IMD system employing the TCC signal transmission techniques disclosed herein. For example, pacemaker 70 could be implanted in the left ventricle instead of in the RV. Furthermore, IMD system 101 may include more than two leadless pacemakers, e.g., RA pacemaker 100, RV pacemaker 70 and a third leadless pacemaker implanted in the left ventricle for providing multi-chamber cardiac pacing for achieving CRT as an example.

RA pacemaker 100 may be implanted in the RA to sense an atrial electrical signal and deliver atrial pacing pulses. RV pacemaker 70 may be implanted in or along the right or left ventricle for sensing a ventricular electrical signal and delivering ventricular pacing pulses. Pacemakers 100 and 70 may be configured to operate cooperatively as a dual chamber pacing and sensing system by communicating via TCC signals to coordinate delivery of atrial-synchronized ventricular pacing pulses.

RV pacemaker 70 may operate as a triggered pacemaker that receives TCC signals from pacemaker 100 and responds to a TCC signal by scheduling and delivering a ventricular pacing pulse. If an intrinsic R-wave is sensed by RV pacemaker 70 before delivery of a triggered, scheduled pacing pulse, the scheduled pacing pulse may be withheld. In this example, RA pacemaker 100 may sense an atrial signal via housing based electrodes 152 and 160, detect an intrinsic P-wave, generate a TCC signal in response to detecting the P-wave, and control a TCC transmitter included in RA pacemaker 100 to transmit the TCC signal. RA pacemaker 100 may schedule an atrial pacing pulse by setting an atrial pacing interval in response to a sensed P-wave or a delivered atrial pacing pulse and deliver the scheduled atrial pacing pulse in response to the atrial pacing interval expiring prior to sensing the next P-wave. The RA pacemaker 100 may generate a TCC signal for transmission to RV pacemaker 70 in response to delivering the atrial pacing pulse. RV pacemaker 70 schedules and delivers a ventricular pacing pulse in response to detecting the transmitted TCC signal. In this way, dual chamber pacing and sensing is achieved.

As described in greater detail below, RA pacemaker 100 may be configured to identify a TCC transmission time interval within a cardiac cycle, a group of cardiac cycles, or a respiration cycle that is characterized by increased transimpedance between the transmitting electrode vector, e.g., electrodes 152 and 160, and the receiving electrode vector, e.g., electrodes 72 and 74, of RV pacemaker 70. RA pacemaker 100 may select a TCC signal transmission time within the identified time interval to transmit a pacing trigger signal as a TCC signal to pacemaker 70. The selected signal transmission time within the identified time interval may be based on a desired AV interval between the intrinsic P-wave or delivered atrial pacing pulse and the subsequently triggered ventricular pacing pulse and inherent system delays.

In some cases, the AV interval between an atrial event, sensed or paced, and the triggered pacing pulse is applied by the transmitting RA pacemaker 100 by selecting the appropriate time for transmitting the trigger signal. The responding RV pacemaker 70 may generate and deliver the ventricular pacing pulse without delay. In other examples, the AV interval may be applied by the receiving RV pacemaker 70 by starting the AV interval in response to detecting the transmitted TCC signal and delivering the ventricular pacing pulse upon expiration of the AV interval. If an intrinsic R-wave is sensed by the RV pacemaker 70 prior to expiration of the AV interval, RV pacemaker 70 may withhold the scheduled ventricular pacing pulse. RV pacemaker 70 may start a VV pacing interval following each sensed R-wave and deliver a ventricular pacing pulse for providing backup ventricular pacing in the absence of a received trigger signal or sensed R-wave prior to expiration of the VV pacing interval.

In some examples, RV pacemaker 70 may be configured to transmit a TCC signal to RA pacemaker 100 to signal the occurrences of sensed R-waves and/or delivered pacing pulses. RA pacemaker 100 may receive the transmitted TCC signals for confirming a ventricular rate and/or verifying receipt of a pacing trigger signal by RV pacemaker 70. As described below, RV pacemaker 70 may transmit a TCC signal to acknowledge receipt of a TCC signal transmitted by RA pacemaker 100 and vice versa. RA pacemaker 100 may use TCC signals received from RV pacemaker 70 (or RV pacemaker 70 may use TCC signals received from RA pacemaker 100) in identifying a TCC transmission interval and selecting a TCC signal transmission time.

In the examples of FIGS. 1 and 2, two or more IMDs may be co-implanted in a patient and communicate via TCC to enable a system level of functionality such as sharing the detection of arrhythmias between devices, synchronized timing of anti-tachyarrhythmia shocks, ATP, and/or post-shock pacing, optimization of the resources (e.g., battery capacity or processing power) available to each device, or sharing or coordination of physiological signal acquisition. It is recognized that numerous examples and applications of TCC in an IMD system may be conceived that may benefit from the TCC signal transmission techniques disclosed herein for providing adaptive timing of the TCC signal transmission to promote transmission at a time of relatively high transimpedance, e.g., when the transimpedance is time-varying due to patient body motion. Techniques described herein for TCC transmission may be used with other IMD systems including other types and locations of IMDs as well as other lead and electrode arrangements.

Figure 3:
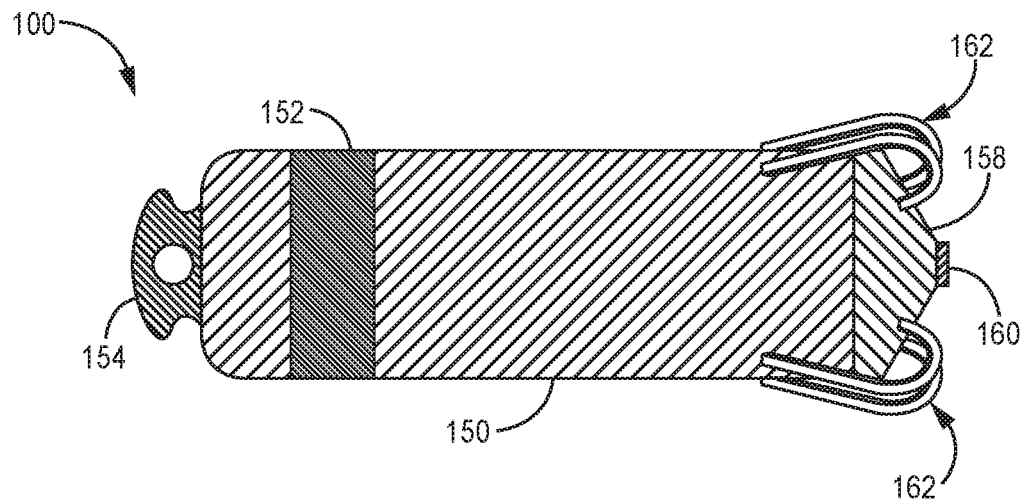
FIG. 3 is a conceptual diagram of a leadless intracardiac pacemaker according to one example.

FIG. 3 is a conceptual diagram of pacemaker 100 according to one example. Pacemaker 100 may be implanted in or along any cardiac chamber as described above. As shown in FIG. 3, pacemaker 100 may be a leadless pacemaker including a housing 150, housing end cap 158, distal electrode 160, proximal electrode 152, fixation member 162, and a delivery tool interface member 154. Housing 150, sealed with end cap 158, encloses and protects the various electrical components within pacemaker 100. Pacemaker 100 is shown including two electrodes 152 and 160 but may include two or more electrodes for delivering cardiac pacing pulses, sensing cardiac electrical signals, and for receiving and/or transmitting TCC signals.

Electrodes 152 and 160 are carried on the housing 150 and housing end cap 158. In this manner, electrodes 152 and 160 may be considered housing-based electrodes. In other examples, one or more electrodes may be coupled to circuitry enclosed by housing 150 via an electrode extension extending away from housing 150. In the example of FIG. 3, electrode 160 is disposed on the exterior surface of end cap 158. Electrode 160 may be a tip electrode positioned to contact cardiac tissue upon implantation and fixation at a pacing site by fixation member 162. Electrode 152 may be a ring or cylindrical electrode disposed along the exterior surface of housing 150. Both housing 150 and housing end cap 158 may be electrically insulating. In some examples, housing 150 is an electrically conductive material, e.g., a titanium alloy or other biocompatible metal or metal alloy. Portions of housing 150 may be coated with a non-conductive material, e.g., parylene, polyurethane, silicone or other biocompatible polymer, to insulate portions of housing 150 not functioning as electrode 152.

Electrodes 160 and 152 may be used as a cathode and anode pair for delivering cardiac pacing pulses and as an electrode vector for receiving and/or transmitting TCC signals. In addition, electrodes 152 and 160 may be used to detect intrinsic electrical signals from the patient's heart 8. In other examples, pacemaker 100 may include three or more electrodes, where any two or more of the electrodes may be selected to form a vector for delivery of electrical stimulation therapy, detecting intrinsic cardiac electrical signals from the patient's heart 8, transmitting TCC signals, and receiving TCC signals. In some examples in which pacemaker 100 includes three or more electrodes, two or more of the electrodes may be selected, e.g., via switches, to form a vector for TCC.

Fixation member 162 may include multiple tines of a shape memory material that retains a preformed curved shape as shown. During implantation, fixation member 162 may be flexed forward to pierce tissue and elastically flex back towards housing 150 to regain their pre-formed curved shape. In this manner, fixation member 162 may be embedded within cardiac tissue at the implant site. In other examples, fixation member 162 may include helical fixation tines, barbs, hooks or other fixation features.

Delivery tool interface member 154 may be provided for engaging with a delivery tool used to advance pacemaker 100 to an implant site. A delivery tool may be removably coupled to delivery tool interface member 154 for retrieving pacemaker 100 back into a delivery tool if removal or repositioning of pacemaker 100 is required.

Figure 4:
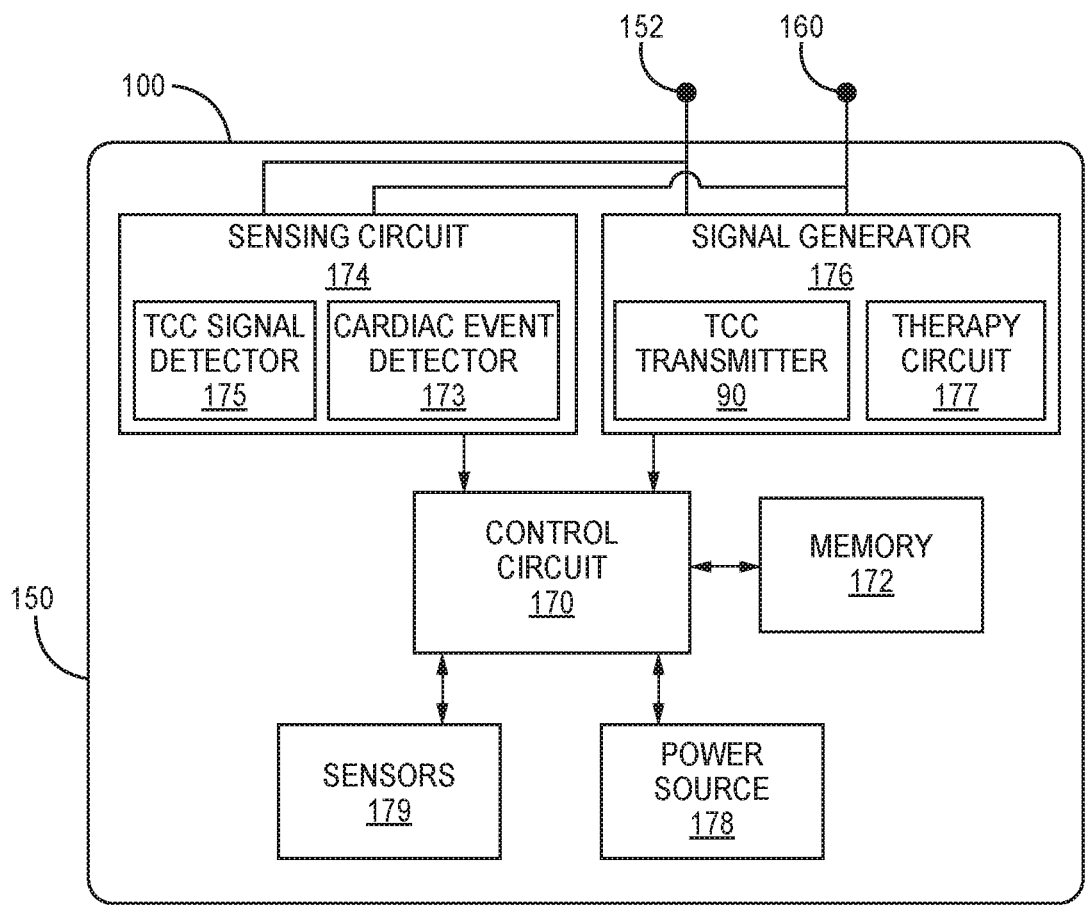
FIG. 4 is a schematic diagram of circuitry that may be included in the pacemaker of FIG. 3 according to one example.

FIG. 4 is a schematic diagram of circuitry that may be enclosed by pacemaker housing 150 of RA pacemaker 100 according to one example. Pacemaker housing 150 may enclose a control circuit 170, memory 172, signal generator 176, sensing circuit 174, and a power source 178. Control circuit 170 may include a microprocessor and/or other control circuitry for controlling the functions attributed to pacemaker 100 herein, such as controlling signal generator 176 to deliver signals via electrodes 152 and 160 and controlling sensing circuit 174 to detect signals from electrical signals received via electrodes 152 and 160. RV pacemaker 70 may include the same or similar circuitry that is adapted to providing ventricular sensing and pacing instead of atrial sensing and pacing, e.g., by programming different control parameters and algorithms used by the control circuit 170 for controlling sensing, pacing and TCC communication functions.

Power source 178 may include one or more energy storage devices, such as one or more rechargeable or non-rechargeable batteries, for providing power to control circuit 170, memory 172, signal generator 176 and sensing circuit 174 as needed. The connections between power source 178 and each of the other circuits 170, 172, 174 and 176 are to be understood from the general block diagram of FIG. 4, but are not shown for the sake of clarity. For example, power source 178 may be coupled to charging circuits included in signal generator 176 for charging capacitors or other charge storage devices included in therapy circuit 176 for producing cardiac pacing pulses. Power source 178 is coupled to TCC transmitter 90 for providing power for generating TCC signals. Power source 178 provides power to processors and other components of control circuit 170, memory 172, and amplifiers, analog-to-digital converters and other components of sensing circuit 174 as examples.

Control circuit 170 communicates with signal generator 176 and sensing circuit 174 for sensing cardiac electrical activity, detecting cardiac rhythms, communicating with other co-implanted IMDs, and controlling delivery of cardiac electrical stimulation therapies in response to sensed cardiac signals and/or received TCC signals as needed. The blocks shown in FIG. 4 as various circuits represent functionality included in pacemaker 100 and may include any discrete and/or integrated electronic circuit components that implement analog and/or digital circuits capable of producing the functions attributed to pacemaker 100 herein. Providing software, hardware, and/or firmware to accomplish the described functionality in the context of any modern IMD system, given the disclosure herein, is within the abilities of one of skill in the art.

Control circuit 170 may execute instructions stored in memory 172 and may control signal generator 176 and sensing circuit 174 according to control parameters and algorithms stored in memory 172, such as various timing intervals, pacing pulse parameters and cardiac event sensing parameters. As described below, control circuit 170 may execute instructions for determining a TCC signal transmission time and control TCC transmitter 90 to transmit a TCC signal at the determined time. Memory 172 may be configured to store a variety of operational parameters, therapy parameters, sensed and detected data, and any other information related to the monitoring, therapy and treatment of patient 12. Memory 82 may store, for example, thresholds and parameters for sensing cardiac signals and detecting arrhythmias and/or therapy parameter values for controlling cardiac pacing pulses. In some examples, memory 82 may also store TCC communications transmitted to and/or received from another device, such as ICD 14, sensor 50 or another pacemaker 70.

Signal generator 176 includes therapy circuit 177 that generates therapeutic pacing pulses delivered via electrodes 152 and 160 under the control of control circuit 170. Signal generator 176 may include charging circuitry (which may include a charge pump as an example), one or more charge storage devices such as one or more capacitors, and switching circuitry that is controlled to electrically couple the charge storage device(s) to an output capacitor coupled to electrodes 160 and 152 to discharge the charge storage devices via electrodes 160 and 152 at an appropriate time to deliver a cardiac pacing pulse. Signal generator 176 further includes a TCC transmitter 90, as described below in conjunction with FIG. 5, for generating TCC signals transmitted via electrodes 160 and 152.

Pacemaker 100 may be configured for sensing cardiac electrical signals, e.g., R-waves or P-waves, and includes a cardiac event detector 173. Intrinsic cardiac electrical events may be detected from an electrical signal produced by the heart and received via electrodes 152 and 160. Cardiac event detector 173 may include filters, amplifiers, an analog-to-digital converter, rectifier, comparator, sense amplifier or other circuitry for detecting cardiac events from a cardiac electrical signal received via electrodes 152 and 160. Under the control of control circuit 170, cardiac event detector 173 may apply various blanking and/or refractory periods to circuitry included in event detector 173 and an auto-adjusting cardiac event detection threshold amplitude, e.g., an R-wave detection threshold amplitude or a P-wave detection threshold amplitude, to the electrical signal received via electrodes 152 and 160. Cardiac event detector 173 may generate a cardiac sensed event signal, e.g., a P-wave sensed event signal or an R-wave sensed event signal, which is passed to control circuit 170 in response to the received cardiac electrical signal crossing the detection threshold amplitude. Control circuit 170 may include one or more escape interval timers or counters for controlling pacing timing intervals, e.g., an AA interval, VV interval or AV interval. An escape interval timer may be reset upon receipt of a cardiac sensed event signal from cardiac event detector 173 or upon delivery of a pacing pulse by therapy circuit 177.

Sensing circuit 174 may further include a TCC signal detector 175 for detecting a TCC signal transmitted from a transmitting device, e.g., ICD 14, sensor 50 (both shown in FIG. 1), or another pacemaker 70 as shown in FIG. 2. A voltage potential may develop across electrodes 152 and 160 in response to current conducted via a tissue pathway during TCC signal transmission. The developed voltage signal may be received and demodulated by TCC signal detector 175 and decoded by control circuit 170. TCC signal detector 175 may include amplifiers, filters, analog-to-digital converters, rectifiers, comparators, counters, a phase locked loop and/or other circuitry configured to detect a TCC signal from a transmitting device. The transmitted TCC signal may be a modulated carrier signal to enable the TCC signal detector to discriminate the TCC signal from other noise, such as electromagnetic interference (EMI). In the case of a modulated carrier signal, TCC signal detector 175 is configured to demodulate the TCC signal and produce a stream of digital bits or a binary analog signal passed to control circuit 170 for decoding of the encoded data. For example, TCC signal detector 175 may include a pre-amplifier and a high-Q filter tuned to the carrier frequency of a carrier signal that is used to transmit TCC signals. The filter may be followed by another amplifier and a demodulator that converts the received signals to a binary signal representing coded data.

The circuitry of TCC signal detector 175 may include circuitry shared with cardiac event detector 173 in some examples. The filters included in TCC signal detector 175 and cardiac event detector 173, however, are expected to operate at different passbands, for example, for detecting different signal frequencies. The TCC signals may be transmitted with a carrier frequency in the range of 33 to 250 kHz, in the range of 60 to 200 kHz, or at 100 kHz as examples. Cardiac electrical signals generated by heart 8 are generally less than 100 Hz, well below the bandwidth of the transmitted TCC signals. In some instances, the TCC transmitter may include circuitry shared with signal generator 176, such that the TCC signals are transmitted using the pacing circuitry of pacemaker 70 and/or transmitted as sub-threshold pacing pulses or pacing pulses that occur during the refractory period of the heart.

Pacemaker 100 may be configured to operate as a triggered pacemaker. TCC signal detector 175 may detect a trigger signal transmitted as a TCC signal transmitted by a transmitting device and pass a trigger detection signal to control circuit 170. Control circuit 170 controls therapy circuit 177 to deliver a cardiac pacing pulse, with or without delay, after detecting the trigger signal. Control circuit 170 may control TCC transmitter 90 to transmit an acknowledgment signal to the transmitting device to confirm receipt of the trigger signal. The acknowledgement signal may be transmitted before or after the pacing pulse is delivered but is generally not transmitted simultaneously.

Control circuit 170 may control TCC transmitter 90 to transmit a TCC signal in response to receiving a sensed cardiac event signal from cardiac event detector 173. In some examples, pacemaker 100 may transmit a TCC signal to another implanted device, e.g., ICD 14, sensor 50, or another pacemaker 70, to communicate the time of cardiac events sensed by pacemaker 100 and/or the time of delivered pacing pulses, which may or may not be delivered in response to a received TCC trigger signal. In still other examples, control circuit 170 may control TCC transmitter 90 to transmit an acknowledgment signal to a transmitting device to confirm receipt of a TCC signal by TCC signal detector 175, which may be a command or other data other than a pacing trigger signal. In some examples, when pacemaker 100 is functioning as a responder, control circuit 170 may control TCC transmitter 90 to transmit a TCC acknowledgment signal to a transmitting device in response to TCC signal detector 175 detecting a received TCC signal to facilitate establishment of a TCC transmission time interval by the transmitting device.

Pacemaker 100 may include other sensors 179 for producing a signal correlated to a physiological event or condition. For example, pacemaker 100 may include an accelerometer that produces a signal correlated to patient activity for use by control circuit 170 for detecting a change in patient activity and controlling a pacing rate delivered by therapy circuit 177. Sensors 179 may include one or more physiological sensor, including but not limited to, a patient activity sensor, posture sensor, oxygen sensor, pressure sensor, acoustical sensor, or the like. In some examples, control circuit 170 may be configured to monitor impedance between electrodes 152 and 160.

In other examples, pacemaker 100 may include fewer or more components than the circuits and components shown in FIG. 4. For instance, pacemaker 100 may include other physiological sensors and/or an RF telemetry circuit for communication with external device 40.

Figure 5:
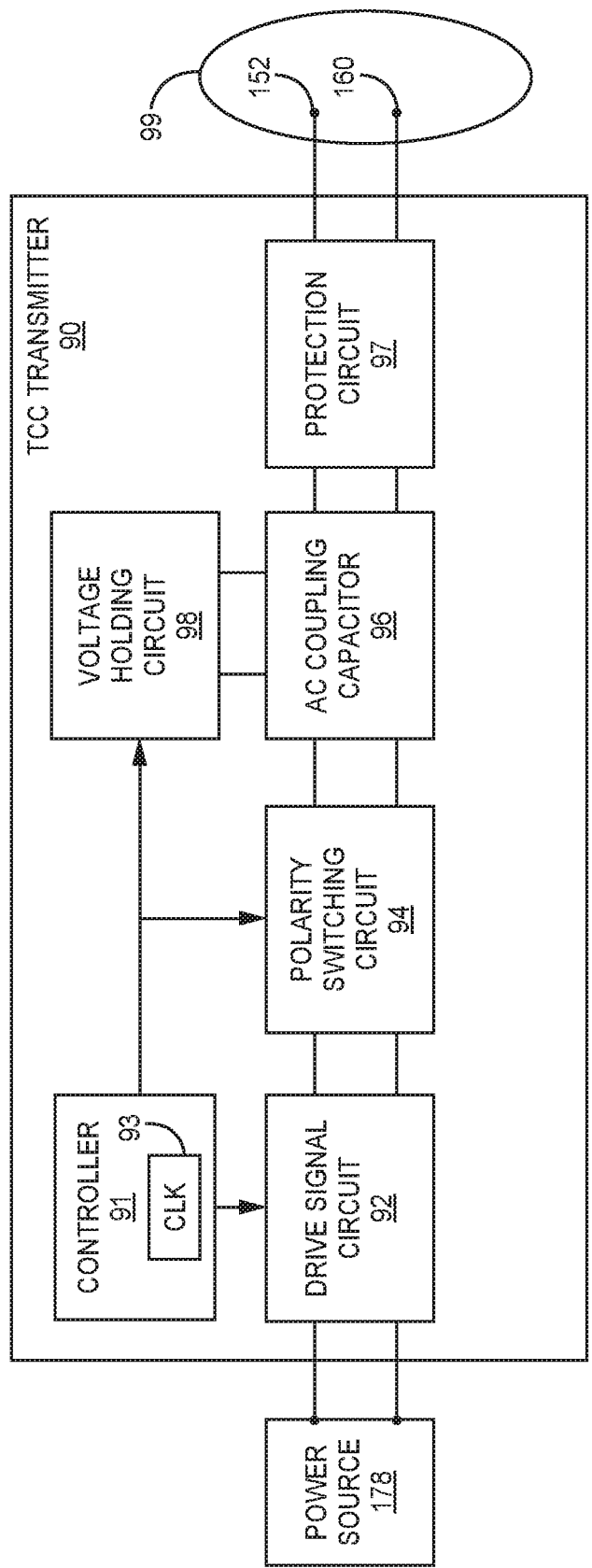
FIG. 5 is a conceptual diagram illustrating an example configuration of a TCC transmitter that may be included in an IMD configured to perform the TCC transmission techniques disclosed herein.

FIG. 5 is a conceptual diagram of a TCC transmitter 90 according to one example. A TCC transmitter 90 may be included in any of the example IMDs described above, such as ICD 14, sensor 50, pacemaker 100 or pacemaker 70. TCC transmitter 90 may be included in both pacemaker 100 provided as a RA pacemaker and in RV pacemaker 70 in FIG. 2 for providing wireless communication between RA pacemaker 100 and RV pacemaker 70 in coordinating dual chamber sensing and pacing in IMD system 101.

TCC transmitter 90 may include a controller 91, drive signal circuit 92, polarity switching circuit 94, alternating current (AC) coupling capacitor 96, protection circuit 97 and voltage holding circuit 98. Power source 178 is shown coupled to TCC transmitter 90 to provide power necessary to generate TCC signals. While the controller 91, drive signal circuit 92, polarity switching circuit 94, AC coupling capacitor 96, protection circuit 97 and voltage holding circuit 98 are shown as discrete circuits by the blocks in FIG. 5, it is recognized that these circuits may include common components or a common circuit may perform the functions attributed to the separate circuit blocks shown in FIG. 5. For example, generating a TCC signal as a carrier signal having a carrier frequency and a peak-to-peak amplitude may be performed by drive signal circuit 92 and polarity switching circuit 94 under the control of controller 91.

Controller 91 may include a processor, logic circuitry, data registers, a clock circuit and/or other circuitry or structures for providing the functionality attributed to controller 91 herein. Controller 91 may include a dedicated clock circuit 93 for generating clock signals used to control the frequency of the transmitted TCC signals. In some examples, TCC transmitter 90 is configured to transmit the TCC signal as a modulated carrier signal using amplitude modulation, frequency modulation, or digital modulation techniques, as examples, such as frequency shift keying (FSK) or binary phase shift keying (BPSK). For example, the clock circuit 93 may be configured to provide a clock signal that may be used to transmit the TCC signal during a transmission session using at least three different frequencies including the carrier signal frequency and high and low frequencies, which may be centered on the carrier signal frequency, for providing FSK modulated signals.

TCC transmitter 90 is shown coupled to a transmitting electrode vector 99 including pacemaker electrodes 152 and 160 in this example. It is to be understood that TCC transmitter 90 may be coupled to one or more TCC transmitting electrode vectors selected from any of the available electrodes coupled to the transmitting device, e.g., via switching circuitry included in signal generator 177. Controller 91 may be configured to switchably connect a transmitting electrode vector 99 to TCC transmitter 90 for transmission of TCC signals, e.g., by controlling switches included in signal generator 177, which may be included in TCC transmitter 90 between AC coupling capacitor 96 and transmitting electrode vector 99, e.g., in protection circuit 97. Controller 91 may select a transmitting electrode vector from among multiple electrodes coupled to the transmitting device, which may include electrodes carried by the housing of the transmitting device, e.g., electrodes 52 and 54 of sensor 50, shown in FIG. 1 a transvenous lead, or a non-transvenous lead, e.g., extra-cardiovascular lead 16 shown in FIG. 1.

Drive signal circuit 92 may include a voltage source and/or a current source powered by power source 178. In one example, drive signal circuit 92 may be an active drive signal circuit generating a balanced, bi-directional drive current signal to balance the return current with the drive current for a net zero DC current injected into the body tissue via transmitting electrode vector 99. In another example, the drive signal circuit 92 may include a charge pump and a holding capacitor that is charged by the charge pump to generate a current signal that is coupled to the transmitting electrode vector 99. In yet another example, drive signal circuit 92 may include a current source that is used to charge a holding capacitor included in drive signal circuit 92.

The drive signal generated by drive signal circuit 92 may be a voltage signal in some examples. In the illustrative examples presented herein, the drive signal circuit 92 generates a current signal to deliver TCC signal current through the transmitting electrode vector 99 having a desired peak-to-peak amplitude, e.g., high enough to produce a voltage signal across a receiving electrode vector that is detectable by the receiving device, which may be another pacemaker 70, sensor 50, ICD 14 or another intended receiving medical device, implanted or external. The peak-to-peak current amplitude is low enough to avoid or minimize the likelihood of stimulation of tissue. A carrier signal that may be generated by drive signal circuit 92 and polarity switching circuit 94 may have a peak-to-peak amplitude in a range from approximately 1 mA to approximately 10 mA, such as approximately 3 mA peak-to-peak. The voltage developed at the receiving electrode vector may be in the range of 0.1 to 100 millivolts peak-to-peak.

Polarity switching circuit 94 receives the drive signal from drive signal circuit 92 and includes circuitry configured to switch the polarity of the drive signal current at a carrier frequency of the TCC signal. For example, polarity switching circuit 94 may include transistors and/or switches configured to switch the polarity of the drive current signal at the frequency of the TCC signal. In some examples, polarity switching circuit includes a respective one or more transistors and/or switches coupled to each of electrode 152 and 160, and the on-off states of the respective transistor(s) and/or switch(es) are alternated to switch the polarity of the TCC signal current between the electrodes at the carrier frequency. As discussed above, the carrier frequency may be approximately 100 kHz. For example, the carrier frequency may be within a range from approximately 33 kHz to approximately 250 kHz.

Controller 91 may be configured to produce a digital input signal to drive signal circuit 92 and/or polarity switching circuit 94 for modulating the TCC carrier signal to encode communication data in the transmitted signal. Controller 91 controls one or both of drive signal circuit 92 and polarity switching circuit 94 to modulate the TCC carrier frequency signal to generate the modulated TCC signal with an amplitude, phase shifts and/or frequency according to the encoding. For example, controller 92 may control polarity switching circuit 94 to toggle the frequency of the carrier signal according to FSK modulation to encode the communication data. In another example, controller 91 may control polarity switching circuit 94 to switch the polarity of the current signal after a desired portion of the carrier frequency cycle length to shift the phase of the AC current signal by 180 degrees (or other selected phase shift) according to BPSK modulation.

Polarity switching circuit 94 is capacitively coupled to the transmitting electrode vector 99 via AC coupling capacitor 96. AC coupling capacitor 96 couples the current signal output from polarity switching circuit 94 to the transmitting electrode vector 99 to inject the current into the conductive body tissue pathway. AC coupling capacitor 96 may include one or more capacitors coupled in series with one or each of the electrodes included in electrode vector 99. AC coupling capacitor 96 is selected to have a minimized capacitance that is based on the frequency and the peak-to-peak current amplitude of the carrier signal being used to transmit TCC signals. As examples, AC coupling capacitor 96 may have a capacitance of at least one nanofarad and up to ten microfarads for coupling a carrier signal having a frequency between 25 kHz and 250 kHz and peak-to-peak current amplitude of 100 microamps to 10 milliamps TCC transmitter 90 may include a voltage holding circuit 98 coupled to AC coupling capacitor 96. The AC coupling capacitor 96 is charged up to a DC operating voltage during the beginning cycles of the carrier signal of a TCC signal. A low frequency artifact may be injected into the conductive tissue pathway during this charging. To minimize or avoid low frequency artifact at the beginning of every TCC signal transmission, voltage holding circuit 98 may be configured to hold AC coupling capacitor 96 at the DC operating voltage between TCC signal transmissions. By holding the AC coupling capacitor 96 at a DC voltage during time intervals between TCC signal transmissions, interference with sensing circuitry that may otherwise occur due to any low frequency artifact injected during charging of the AC coupling capacitor 96 to the DC operating voltage is minimized or avoided. Examples of voltage holding circuit 98 and methods of use are generally disclosed in U.S. patent application Ser. No. 16/203,939 (Peichel, et al.), incorporated herein by reference in its entirety.

The TCC transmitter 90 may include protection circuit 97 that allows the delivery of the TCC signal via electrodes coupled to other IMD circuitry but protects the TCC transmitter 90 and other circuitry from voltages that may develop across the electrodes, e.g., during a CV/DF shock delivered by ICD 14 or an external defibrillator as well as high voltages that may develop across the TCC transmitting electrode vector 99 during other situations such as an electrocautery procedure or magnetic resonance imaging. Protection circuit 97 may be coupled between drive signal circuit 92 and the transmitting electrode vector 99, e.g., between AC coupling capacitor 96 and electrodes 152 and 160. In some examples, protection circuit 97 may include circuitry before and/or after AC coupling capacitor 96. Protection circuit 97 may include, as examples, capacitors, inductors, switches, resistors, and/or diodes. Examples of TCC signal generation and protection circuitry that may be utilized in conjunction with the signal transmission techniques disclosed herein are generally described in U.S. Pat. No. 9,636,511 (Carney, et al.), incorporated herein by reference in its entirety.

TCC transmitter 90 may be controlled by control circuit 170 to transmit TCC signals at transmission times that are selected and adaptively adjusted to coincide with time intervals of increased transimpedance between the transmitting electrode vector 99 and a receiving electrode vector. As described below, control circuit 170 of pacemaker 100 may control transmitter 90 to transmit TCC signals at multiple time points of a cardiac cycle, multiple time points within a portion of a cardiac cycle, and/or during multiple cardiac cycles to establish a TCC transmission window as a time interval coinciding with a higher transimpedance than the transimpedance that may occur outside the TCC transmission window. The control circuit 170 monitors for responses to the transmitted TCC signals by the receiving device and establishes the TCC transmission window, also referred to herein as "transmission window," based on at least one response performed by the receiving device and detected by the transmitting device. After the TCC transmission window is established, control circuit 170 may determine a TCC transmission time point within the TCC transmission window to begin transmitting a TCC signal. Control circuit 170 controls transmitter 90 to begin transmitting a pending TCC signal at the transmission time point during one or more cardiac cycles as needed.

Figure 6:
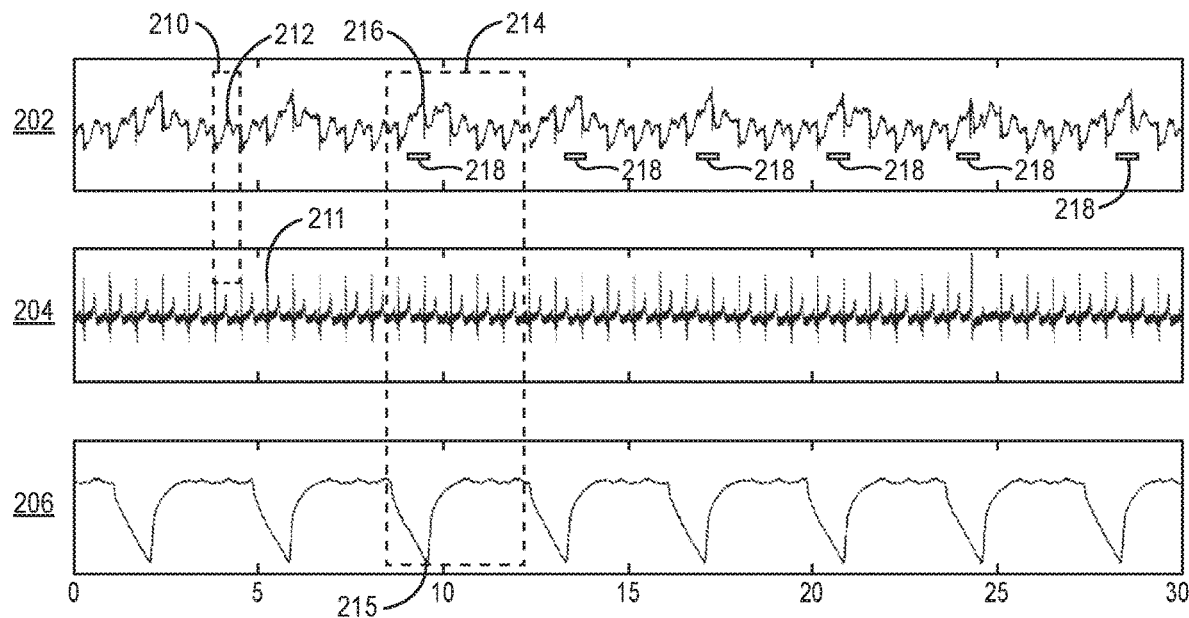
FIG. 6 is a recording of a transimpedance signal between a transmitting IMD and a receiving device acquired simultaneously with an ECG signal and an airway pressure signal.

FIG. 6 is a recording of the transimpedance 202 of a TCC pathway acquired simultaneously with an ECG signal 204 and an airway pressure signal 206. The transimpedance 202 of the TCC pathway may be determined by measuring the voltage at a receiving electrode vector, e.g., electrodes 72 and 74 of pacemaker 70, during transmission of a known TCC current signal from a transmitting electrode vector, e.g., electrodes 152 and 160 of pacemaker 100. Transimpedance 202 is observed to vary cyclically with both the cardiac cycle 210 and the respiratory cycle 214.

In this example, the transimpedance 202 reaches a local maxima 212 during each cardiac cycle 210 prior to the R-wave 211, e.g., during ventricular diastole. Transimpedance 202 reaches a cyclical maximum 216 during each respiratory cycle 214 near peak inspiration 215 (when airway pressure is lowest). Thus, transimpedance 202 is maximized on a cyclical basis during ventricular diastole near each peak inspiration in this example. The time of relative increases in transimpedance during a cardiac or respiratory cycle may differ between IMD systems and configurations and may be dependent on patient posture among other factors. Control circuit 172 may be configured to establish a transmission window 218 corresponding to relatively increased or maximized transimpedance during ventricular diastole and near peak inspiration of the respective cardiac and respiratory cycles.

Transmission window 218 may be based on detecting one or more responses from the receiving device, e.g., pacemaker 70, following transmission of multiple TCC signals at different time points during the cardiac and/or respiratory cycles and determining a time window based on the one or more responses from the receiving device. Transmission window 218 may be defined based on a starting time determined by the transmitting device in response to detecting one or more expected response(s) from the receiving device and may have an open-ended or predetermined duration. In other examples, the end time or duration of the transmission window 218 may be determined based on detected responses from the receiving device and may encompass at least one local maxima of transimpedance 202. The duration of the transmission window may take into account the expected time required to transmit a TCC signal, which may include one data bit, one data byte, a data packet or datagram including multiple data bytes, or multiple data packets or datagrams. In the example shown, transmission window 218 extends less than one cardiac cycle near peak inspiration 215. In other examples, the transmission window 218 may be established to extend over an entire cardiac cycle or more than one cardiac cycle, e.g., at least two cardiac cycles, that coincide with peak inspiration 215 of the respiratory cycle 214. In still other examples, a transmission window 218 may be scheduled during each cardiac cycle, to enable transmission during every cardiac cycle on a beat by beat basis or as needed. The frequency of transmission windows 218 (e.g., once per cardiac cycle 210 or once per respiration cycle 214) may depend on how often communication between the transmitting and receiving devices is needed. For example, if RV pacemaker 70 is a triggered pacemaker, RA pacemaker 100 may transmit a TCC trigger signal every cardiac cycle to trigger ventricular pacing pulses. Alternatively, RA pacemaker 100 may transmit a TCC trigger signal less frequently than every heartbeat. For instance, in response to detecting one trigger signal, RV pacemaker 70 may deliver pacing pulses at a fixed rate until a new trigger signal is detected. Techniques for establishing a transmission window 218 are described below in conjunction with FIG. 8.

After establishing time window 218, control circuit 172 may control TCC transmitter 90 to transmit TCC signals during each time window 218 or less often, e.g., every other time window 218 or on an as needed. In some examples, such as a pacing trigger signal sent from RA pacemaker 100 to RV pacemaker 70, a TCC signal may be transmitted entirely within the transmission window 218. The TCC signal may be 8 to 50 ms, for example, and the TCC time window 218 may be 100 to 500 ms or more. In other examples, if a large number of data bytes or multiple data packets are being transmitted during a transmission session, TCC transmitter 90 may be controlled to transmit the data bytes over multiple time windows 218 if transmission cannot be completed within a signal time window 218.

Figure 7:
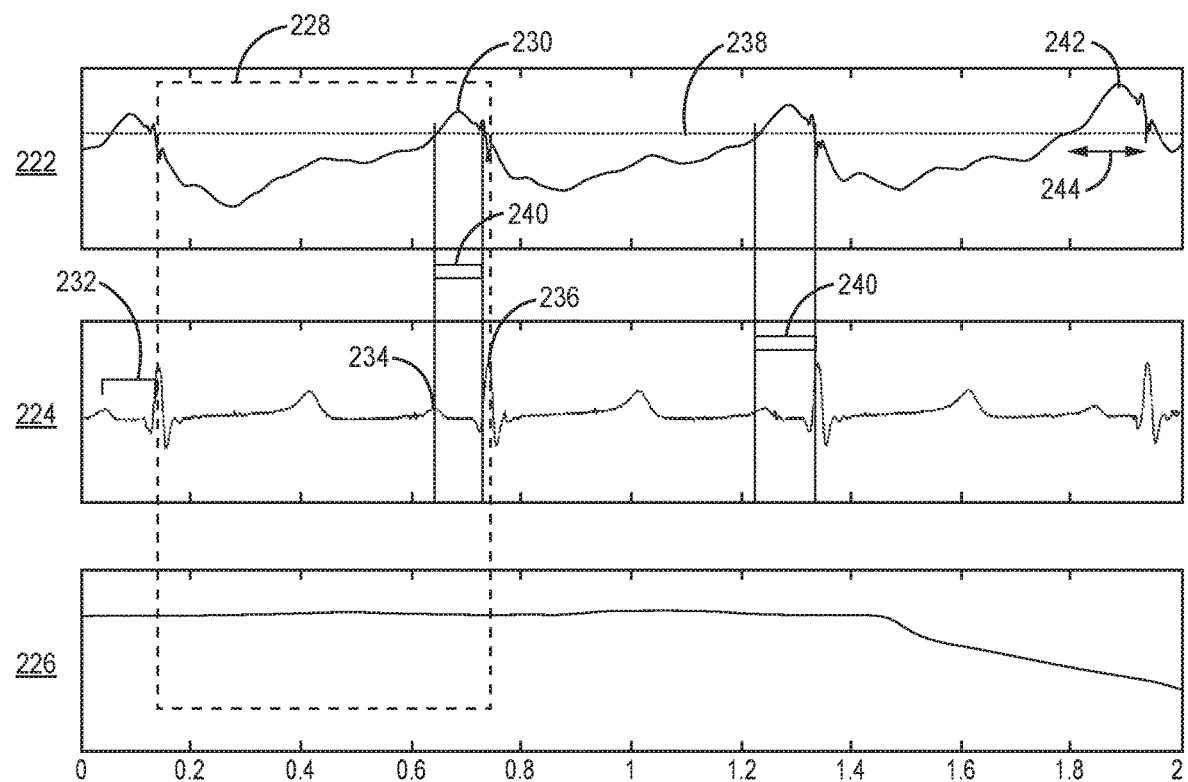
FIG. 7 is a recording of the transimpedance between a TCC transmitting electrode vector and a receiving electrode vector.

FIG. 7 is a recording of the transimpedance 222 between a TCC transmitting electrode vector and a receiving electrode vector. Transimpedance 222 is shown with simultaneously recorded ECG signal 224 and airway pressure signal 226 over a higher resolution time scale than FIG. 6. In the example of FIG. 7, the transimpedance 222 is clearly observed to reach a peak 230 during each cardiac cycle 228, prior to each R-wave 236, approximately corresponding to the time period of ventricular diastole. The control circuit 172 of RA pacemaker 100 may establish TCC transmission window 240 based on responses received from RV pacemaker 70 during repetitive TCC signal transmissions at different times in the cardiac cycle to identify a time window 240 correlated to a relative increase in transimpedance and reliable TCC reception. In the example shown, the TCC transmission window 240 corresponds substantially to ventricular diastole and the PR interval 232. In other cases, however, the maximum transimpedance during a cardiac cycle may occur at any time during the cardiac cycle and may depend on numerous factors such as IMD implant location and orientation, individual patient anatomy, and patient posture as examples.

Control circuit 170 may control transmitter 90 to transmit TCC signals scanning the cardiac cycle 228, for example from one R-wave 236 to the next R-wave or from one P-wave 234 to the next P-wave. In other examples, control circuit 170 may control transmitter 90 to transmit TCC signals to scan a portion of the cardiac cycle 228, e.g., PR interval 232 or an RP interval. For instance, a TCC signal may be transmitted at 1 ms intervals, 5 ms, 10 ms interval, 20 ms intervals or other time interval throughout the cardiac cycle 228. In other examples, a TCC signal may be transmitted continuously, e.g., as an unmodulated or modulated carrier signal, over a cardiac cycle, a portion of a cardiac cycle, or other time period of interest.

Control circuit 170 may be configured to monitor for an expected response from the receiving device following transmission of TCC signals. An expected response may include receiving a TCC acknowledgement signal transmitted from the receiving device, detecting a pacing pulse delivered by the receiving device, receiving an encoded TCC data signal transmitted by the receiving device back to the transmitting device, or any combination thereof. An encoded TCC data signal may include data requested by the transmitting device, such as physiological signal data, or data indicating the time window of highest transimpedance (or highest voltage signal) as determined by the receiving device, or any combination thereof. Based on detecting at least one or more expected responses from the receiving device, control circuit 170 may establish TCC transmission window 240.

In one example, control circuit 170 controls transmitter 90 to transmit a TCC signal continuously or at multiple time points during a PR interval or an entire cardiac cycle and the receiving device e.g., RV pacemaker 70, monitors the voltage received at the receiving electrode vector. The control circuit of RV pacemaker 70 may analyze the voltage signal to detect peak amplitude 230 or a crossing of a voltage threshold to determine a time interval during the cardiac cycle or portion thereof during which the received voltage signal is relatively increased for a given transmitted current amplitude of the TCC signal. The voltage and a corresponding threshold may be used as a surrogate for transimpedance 222 and a transimpedance threshold 238, respectively. For a fixed peak-to-peak amplitude of the injected current signals transmitted over a test interval, a time point or time interval corresponding to an increased or peak voltage amplitude may be identified. In one example, RV pacemaker 70 may transmit a TCC signal to RA pacemaker 100 at the time of a positive threshold crossing and at the time of a negative threshold crossing to indicate time window 240. Alternatively, an encoded TCC signal may be transmitted during a cardiac cycle at the time of a positive threshold crossing with time window duration information encoded in the modulated TCC signal. In still another example, a modulated multi-bit data signal encoded with the starting time, ending time, and/or duration of the transmission window 240 relative to a sensed R-wave or other fiducial time point may be transmitted back to the transmitting device.

As seen in FIG. 6, the respiratory cycle causes cyclical changes of the transimpedance 222 such that during some cardiac cycles, e.g., coincident with inspiration, the transimpedance between the transmitting and receiving electrode vectors reaches a higher maximum peak 242. As a result, the transimpedance 222 may be greater than a threshold transimpedance 238 for a longer time interval 244 during some cardiac cycles than during other cardiac cycles. This variation from one cardiac cycle to the next due to respiratory effects may be accounted for in establishing the TCC transmission window 240 by transmitting test TCC signals over multiple cardiac cycles and averaging results or selecting the narrowest time interval over which transimpedance (or the received voltage signal) is greater than a selected threshold or determined to be relatively increased compared to other portions of the cardiac cycle.

In other examples, RA pacemaker 100 may transmit a TCC signal as a pacing trigger signal at various time points in the PR interval over multiple cardiac cycles. RA pacemaker 100 may monitor for a ventricular pacing pulse or far field evoked R-wave from the atrial cardiac signal following each transmitted pacing trigger signal to identify a time point at which pacing pulses reliably occurred at an expected AV interval in response to the transmitted TCC signal.

Figure 8:
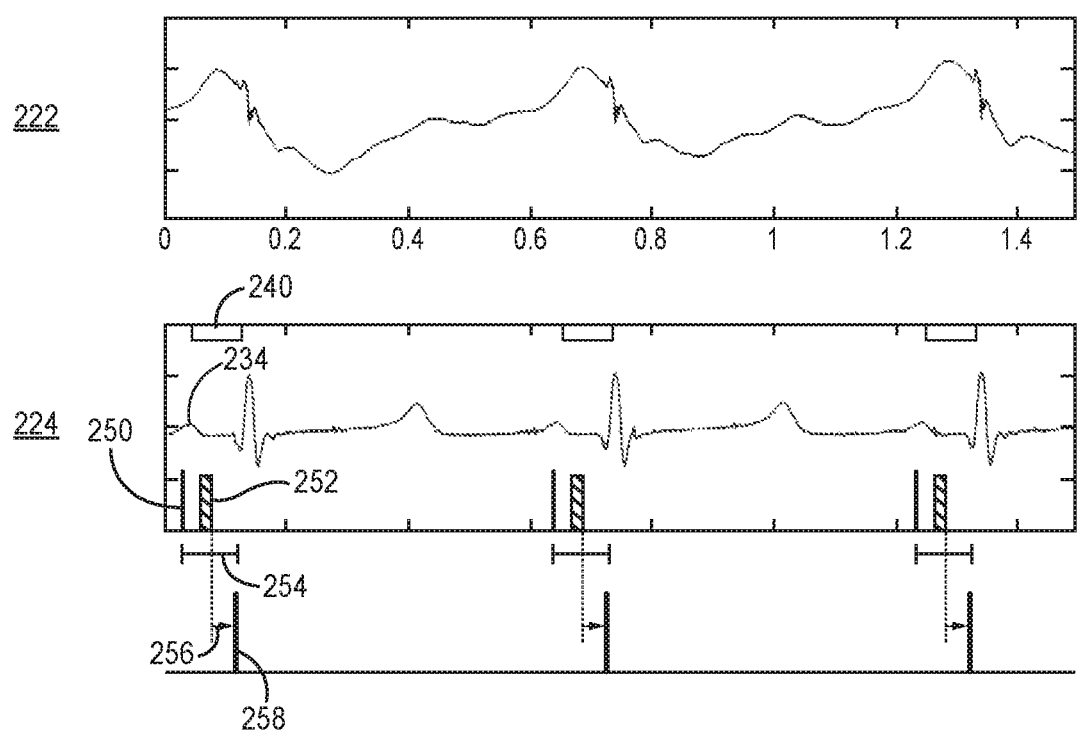
FIG. 8 is a schematic diagram of operations performed by a right atrial pacemaker and a right ventricular pacemaker for achieving dual chamber pacing and sensing using TCC.

FIG. 8 is a schematic diagram of operations performed by RA pacemaker 100 and RV pacemaker 70 for achieving coordinated dual chamber pacing and sensing using TCC. In FIG. 8, the recording of the transimpedance signal 222 and ECG signal of 224 of FIG. 7 are shown. After establishing TCC transmission window 240, RA pacemaker 100 and RV pacemaker 70 may communicate via TCC during the established transmission window 240 to control atrial-synchronized ventricular pacing. Sensing circuit 174 of RA pacemaker 100 detects a P-wave 234 and passes a P-wave sensed event signal 250 to control circuit 170. Control circuit 170 may start TCC transmission window 240 at a predetermined time, e.g., at a predetermined time interval after P-wave sensed event signal 250. Control circuit 170 controls transmitter 90 to transmit a TCC pacing trigger signal 252 at a selected transmission time during TCC transmission window 240.

In response to detecting the TCC pacing trigger signal 252, RV pacemaker 70 delivers a ventricular pacing pulse 258. RV pacemaker 70 may wait for a delay time 256 after detecting TCC pacing trigger signal 252. TCC pacing trigger signal 252 may be transmitted at the expiration of an AV pacing interval 254 set by control circuit 170, and RV pacemaker 70 may deliver pacing pulse 258 upon detecting TCC pacing trigger signal 252 without delay. In other examples, RA pacemaker 100 may transmit TCC pacing trigger signal 252 after a portion of AV interval 254 has expired. RV pacemaker 70 may deliver ventricular pacing pulse 258 after a delay 256 equal to the remaining portion of the AV interval 254. In yet another example, RA pacemaker 100 may transmit the TCC pacing trigger signal immediately upon detecting P-wave 234, and RV pacemaker 70 may detect the TCC pacing trigger signal 252 and wait for a delay 256 equal to a desired AV interval 254 before delivering ventricular pacing pulse 258.

The time of TCC trigger signal 252 during AV interval 254 and any subsequently necessary delay 256 applied by RV pacemaker 70 to deliver a ventricular pacing pulse 258 at the desired AV interval 254 will depend on the timing of the TCC transmission window 240 relative to P-wave 234 and any inherent system delays. In some examples, TCC transmission window 240 may start earlier than P-wave 234 such that TCC pacing trigger signal 252 may be transmitted upon P-wave sensed event signal 250. In other examples, TCC transmission window 240 may start later than P-wave sensed event signal 250 and the start of AV pacing interval 254 such that TCC pacing trigger signal 252 is delivered during AV pacing interval 254. In some examples, the transmitted TCC pacing trigger signal 252 generated by transmitter 90 may include a modulated carrier signal that is positively detected by RV pacemaker. The modulated trigger signal may encode data to communicate to RV pacemaker 70 the delay time 256 required before delivery of ventricular pacing pulse 258.

Figure 9:
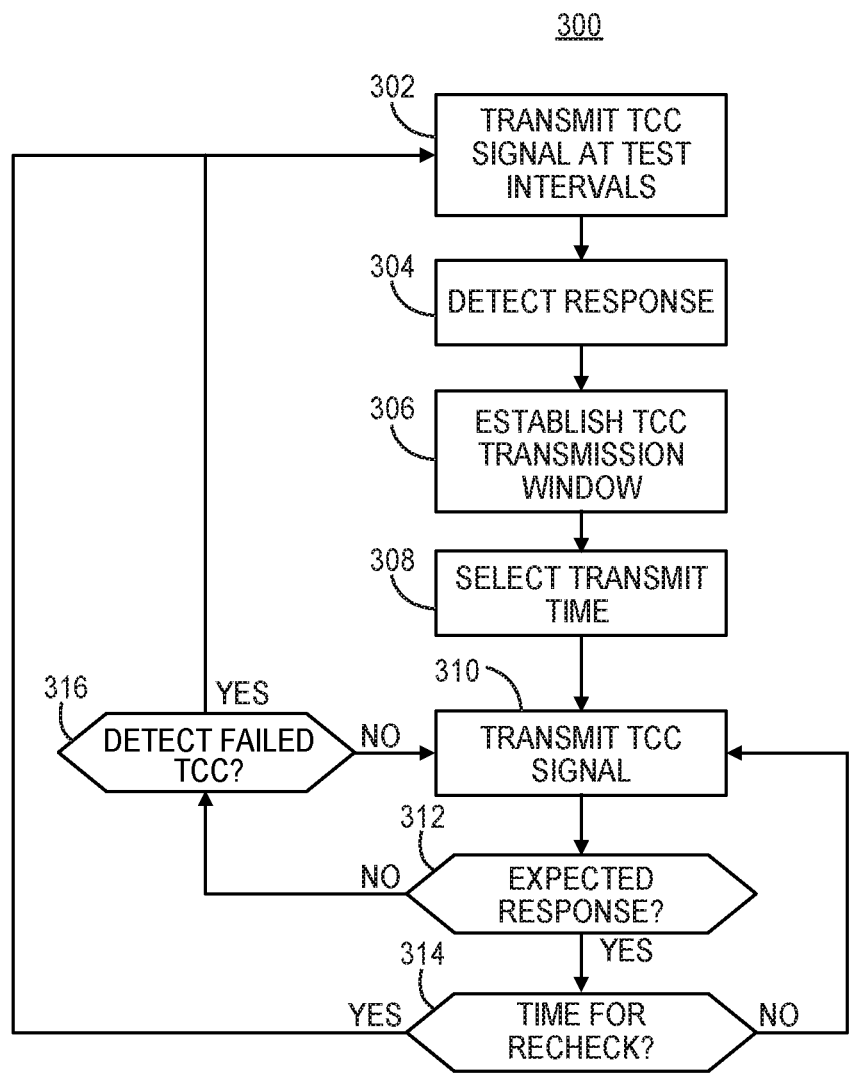
FIG. 9 is a flow chart of a method for controlling TCC signal transmission according to one example.

FIG. 9 is a flow chart 300 of a method for controlling TCC signal transmission according to one example. At block 302, the transmitting device, which may be operating as a control device, such as an ICD 14, sensor 50, or RA pacemaker 100, may transmit a TCC test signal repeatedly at multiple test intervals over a transmission test period, e.g., over one or more cardiac cycles, over a portion of a cardiac cycle, over at least one respiratory cycle, or over a portion of a respiratory cycle. The TCC test signals are transmitted to a receiving device, which may be operating as a responder. In other examples, a TCC signal may be transmitted as a continuous modulated carrier signal for one or more cardiac cycles. The modulated carrier signal may be an FSK modulated signal including alternating time intervals of a high frequency and low frequency, e.g., alternating time intervals of 85 kHz and 115 kHz for a 100 kHz carrier frequency. In another example, the modulated carrier signal may be a BPSK modulated signal, including one or more phase shifts. The phase shifts may be charge balanced, 180 degree phase shifts as described in U.S. patent application No. 16/202,418 (Roberts, et al.), incorporated herein by reference in its entirety.

At block 304, the transmitting device detects at least one response performed by the receiving device. In illustrative examples that follow, the transmitting device is RA pacemaker 100 and the receiving device is RV pacemaker 70. In other examples, however, any of the examples of IMDs described above may operate as the transmitting or the receiving device during a process performed for establishing a TCC transmission window for promoting TCC transmission during a time interval that is correlated to or at least includes a maximized or relatively increased transimpedance between the transmitting and receiving electrode vectors during the transmission period being tested.

Transimpedance for a selected transmitting electrode vector and receiving electrode vector is the same for both directions of TCC signal transmission, all else being equal. In other words, if the receiving device transmits a signal back to the transmitting device, the transimpedance at a given time in the cardiac and respiratory cycles is expected to be same, given a constant patient activity and posture. As such for a given set of transmitting and receiving electrode vectors, the optimal TCC transmission window within a transmission test period, e.g., within one cardiac cycle or within one respiratory cycle, is based on evidence of increased transimpedance during the transmission test period and need only be determined for TCC signal transmissions in one direction; the determined TCC transmission window will be optimal for TCC transmissions in both directions.

If a transmitted TCC signal is successfully received by the RV pacemaker 70 operating as the receiving device, RV pacemaker 70 may perform a response to the received TCC signal that is detected by the RA pacemaker 100 operating as the transmitting device at block 304. In one example, the response is a TCC confirmation or acknowledgment signal transmitted by RV pacemaker 70 to RA pacemaker 100. If multiple TCC signals are being transmitted at predetermined time intervals through the cardiac cycle, or starting from a detected P-wave, the first acknowledgment signal received from RV pacemaker 70 by RA pacemaker 100 indicates the first successful receipt of the TCC signals being transmitted at test intervals.

Control circuit 170 of RA pacemaker 100 may establish the start of the TCC transmission window based on the time of the earliest acknowledgment signal received from RV pacemaker 70 at block 306. In some examples, the duration of the TCC signal may be predetermined, e.g., based on clinical data, or communication time limits imposed by the particular clinical application. For example, if RA pacemaker 100 is transmitting signals at test intervals for determining an optimal TCC transmission window, the TCC transmission window cannot extend later than a desired AV pacing interval after a sense P-wave or delivered atrial pacing pulse. In one example, the TCC transmission window is set to start at the time of the earliest acknowledgment signal after a sensed P-wave or delivered atrial pacing pulse and extends for a maximum interval that is defined as a percentage of the currently programmed AV pacing interval.

In another example, after receiving the earliest acknowledgment signal from RV pacemaker 70, RA pacemaker 100 may continue to monitor for acknowledgment signals sent back from RV pacemaker 70 in response to each detection of a TCC signal transmitted at the test intervals. The latest acknowledgement signal after the earliest acknowledgment signal may be determined and used to establish the end of the TCC transmission window at block 306.

In other examples, RV pacemaker 70 may monitor the voltage signal amplitude over one or more cardiac cycles and determine a time window within the cardiac cycle during which the highest voltage signal amplitude, correlated to the increased transimpedance, is detected. For instance, RV pacemaker 70 may transmit a TCC acknowledgment signal in response to the first TCC signal detected then start monitoring the received voltage until a TCC signal is no longer detected. RV pacemaker 70 may identify a maximum peak voltage signal during the time interval TCC signals were being detected and determine a time window over which the voltage signal is greater than a predetermined percentage, e.g., greater than 80%, 50% or other percentage, of the maximum peak voltage signal detected. The control circuit of the RV pacemaker 70 may control TCC transmitter 90 of RV pacemaker 70 to generate a TCC signal modulated to encode the start and end time of the time window, e.g., relative to the earliest transmitted TCC acknowledgment signal. RV pacemaker 70 transmits the timing information to RA pacemaker 100. Control circuit 170 of RA pacemaker 100 may establish the TCC transmission window based on the timing information decoded from the TCC signal received from RV pacemaker 70.

In another example, the RA pacemaker 100 may transmit a TCC signal requesting the time window duration at a time during the next cardiac cycle corresponding to the time of the first acknowledgment signal received from RV pacemaker 70 on the preceding cardiac cycle. RV pacemaker 100 may respond to the request by transmitting a TCC signal having a duration of the time window determined to encompass the maximum peak voltage signal (as evidence of the increased transimpedance during the cardiac cycle or other transmission test period). RA pacemaker 100 may detect the requested signal transmitted from RV pacemaker 100, determine its time duration, and establish the TCC transmission window at block 306 based on the time of the earliest acknowledgment signal and the requested time window duration.

In other examples, the transmitting device may transmit a command or request to the receiving device and detect the response at block 304 as an appropriate response to the command or request. If the appropriate response is detected, the transmitting device confirms that the transmitted TCC signal was successfully received. The command or request may be transmitted at multiple time points over one cardiac cycle. Alternatively, the command or request may be transmitted once during each cardiac cycle but at a different time point within each cardiac cycle. The time point(s) that resulted in an expected response performed by the receiving device and detected by the transmitting device may be used in establishing the TCC transmission window at block 306. In some examples, the transmitted command or request may be a pacing trigger signal. RA pacemaker 100 (or other transmitting device) may detect the expected response by detecting a delivered pacing pulse or an evoked R-wave occurring at an expected time after the pacing trigger signal. In other examples, the transmitted command or request may be a request for data.

After establishing the TCC transmission window at block 306, RA pacemaker 100 (or other transmitting device) selects a transmit time during the TCC transmission window for transmitting TCC signals, e.g., a pacing trigger signal. The transmit time may be selected based on a desired AV pacing interval and inherent system delays required for generating the pacing trigger signal, detecting the pacing trigger signal by the RV pacemaker 70, and generating a subsequent pacing pulse. In other examples, the selected transmit time may be used for transmitting data or other communication signals and may not be dependent on a pacing interval.

At block 310, RA pacemaker 100 transmits a TCC signal as needed at the selected transmit time. RA pacemaker 100 may monitor for an expected response at block 312. The expected response may be a ventricular pacing pulse at an expected time following a transmitted pacing trigger signal. RA pacemaker 100 may be configured to detect the far field pacing pulse or the far field R-wave at the expected AV interval following a sensed P-wave or delivered atrial pacing pulse (or at an expected portion of the AV interval following the pacing trigger signal).

If RA pacemaker 100 does not detect an expected response to a transmitted signal, a failed transmission may be detected at block 316. RA pacemaker 100 may determine if the expected response has not been detected a threshold number of times following TCC signal transmissions. The threshold number of TCC signals transmitted without detecting an expected response may be as few as one and may depend on the criticality of the TCC transmission in providing coordinated patient monitoring and therapy delivery. If a threshold number of TCC signals have been transmitted without detecting an expected response, RA pacemaker 100 may detect failed TCC at block 316.

Criteria for detecting failed TCC at block 316 may require that less than N out of M transmissions are confirmed based on detecting an expected response. In some cases, as few as one expected response detected out of a predetermined number of TCC signal transmissions may be deemed successful. For example, a TCC signal may be transmitted once per cardiac cycle or once per respiratory cycle and as long as transmission is confirmed based on detecting an expected response at least once out of every four, eight or other predetermined number of TCC signal transmissions, TCC failure is not detected. The control circuit of RA pacemaker 100 may be configured to transmit a TCC signal at a selected transmit time during each cardiac cycle and monitor for an expected response from the receiving device to each one of the TCC signals transmitted at block 312. The RA pacemaker 100 may detect successful TCC transmission in response to an expected response being detected a single time from the receiving device during a predetermined number of the cardiac cycles, e.g., within the last six, eight, twelve or other predetermined number of cardiac cycles.

For instance, the RA pacemaker 100 may transmit a TCC signal at a selected transmit time corresponding to a desired AV interval to trigger RV pacemaker 70 to deliver a ventricular pacing pulse. RV pacemaker 70 may be configured to continue delivering ventricular pacing pulses at a fixed rate in the absence of a detected TCC signal. If a new TCC signal is detected, the RV pacemaker 70 may deliver a ventricular pacing pulse at an adjusted time interval according to the new TCC signal. Since adjustment of the AV interval is not necessarily critical on a beat-by-beat basis, because the heart rate may change gradually over a series of heart beats, adjustment of the AV interval within a time interval of several heart beats may be acceptable. Therefore, as long as the TCC signal is received at least once every 8 cardiac cycles, as an example, control of atrial-synchronized ventricular pacing may be acceptable. If RA pacemaker 100 does not detect at least one expected response performed by the RV pacemaker 70 after transmitting eight TCC signals, failed TCC may be detected at block 316. The expected response may be an acknowledgement signal transmitted as a TCC signal back to RA pacemaker 100 or detection of a ventricular pacing pulse or evoked far-field R-wave by RA pacemaker 100 at an adjusted time interval.

In response to detecting failed TCC at block 316, RA pacemaker 100 may repeat transmission of TCC signals at test intervals at block 302 to re-establish the TCC transmission window. If failed TCC detection criteria are not met at block 316, RA pacemaker 100 may continue transmitting TCC signals at the selected transmission time at block 310. In some examples, even if a required ratio of the expected responses to transmitted TCC signals are being detected (such that failed TCC is not detected at block 316), control circuit 170 may determine if it is time to recheck the TCC transmission window to ensure that the selected transmission time is still within the optimal transmission time. Control circuit 170 may determine that it is time to recheck the TCC transmission window based on a time of day, an elapsed time period since the last time the TCC transmission window was established, a change in heart rate, or a detected change in a physiological signal received from sensors 179. For example, pacemaker 100 may be configured to monitor patient posture and/or patient activity. Detection of a change in patient body posture or a detected change in patient activity may trigger a TCC transmission test for re-establishing the TCC transmission window. In other examples, the transmitting device may be configured to detect a change in respiration rate (e.g., based on a thoracic impedance signal), a change in tissue or blood oxygen saturation, or other event or condition that may be correlated to a change in the timing of the maximum transimpedance between the transmitting and receiving electrode vectors.

If a condition for triggering a recheck of the TCC transmission window is detected at block 314, control circuit 170 initiates transmission of TCC signals at test intervals by transmitter 90 at block 302. If a condition for triggering a recheck is not detected, control circuit 170 continues to control transmitter 70 to transmit TCC signals at the selected transmission time.

Figure 10:
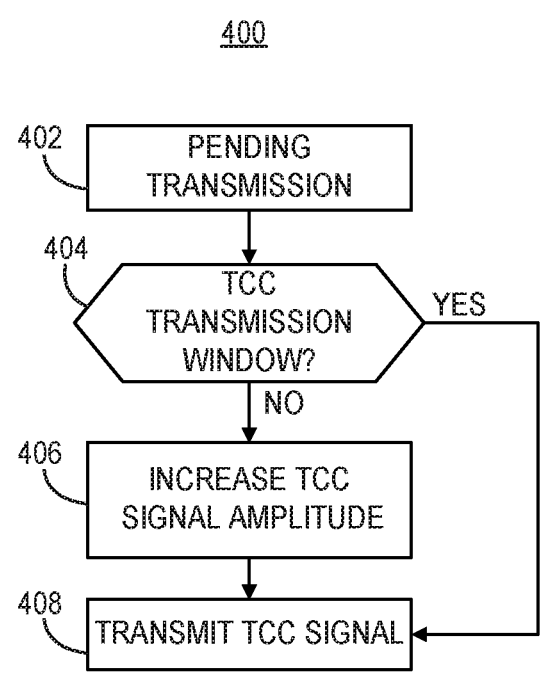
FIG. 10 is a flow chart of a method for controlling transmission of TCC signals according to another example.

FIG. 10 is a flow chart 400 of a method for controlling transmission of TCC signals according to another example. At block 402, the TCC transmitter 90 may determine that a TCC transmission is pending. At block 404, controller 91 of TCC transmitter 90 may determine if the previously established TCC transmission window is enabled. The TCC transmission window may be previously established using the techniques described above. The control circuit of the transmitting device, e.g., control circuit 170 of RA pacemaker 100, may pass timing signals to TCC transmitter 90 when the TCC transmission window is active based on a starting timing signal and an ending timing signal. TCC transmitter 90 may determine that the TCC transmission window is active during the time interval after receiving a starting timing signal and before receiving an ending timing signal.

If the TCC transmission window is active, transmitter 90 may transmit the TCC signal at block 408. If the TCC transmission window is not active ("no" branch of block 404), the controller 92 of transmitter 90 may control the drive signal circuit 92 to increase the amplitude of the drive current signal at block 406. TCC transmitter 90 may transmit the TCC signal with an increased power at block 408 outside the TCC transmission window. For example, the peak-to-peak current amplitude of the carrier signal produced by drive signal circuit 92 and polarity switching circuit 94 may be increased at block 406 to transmit a higher amplitude current signal outside the TCC transmission window, thereby increasing the likelihood of successful TCC signal transmission. In some instances, TCC signal transmission may be delayed until a TCC transmission window is started. In other instances, immediate TCC signal transmission may be required. By increasing the amplitude of a TCC signal, TCC signal transmission may occur outside the TCC transmission window with a high likelihood of success. Transmitter 90 may be configured to adjust the power of a TCC signal generated by drive signal circuit 92 and polarity switching circuit 94, e.g., by increasing the peak-to-peak carrier signal current amplitude, based on the timing of the TCC signal transmission relative to an established TCC transmission window or the determined time of maximum peak transimpedance during a cardiac and/or respiratory cycle.

Figure 11:
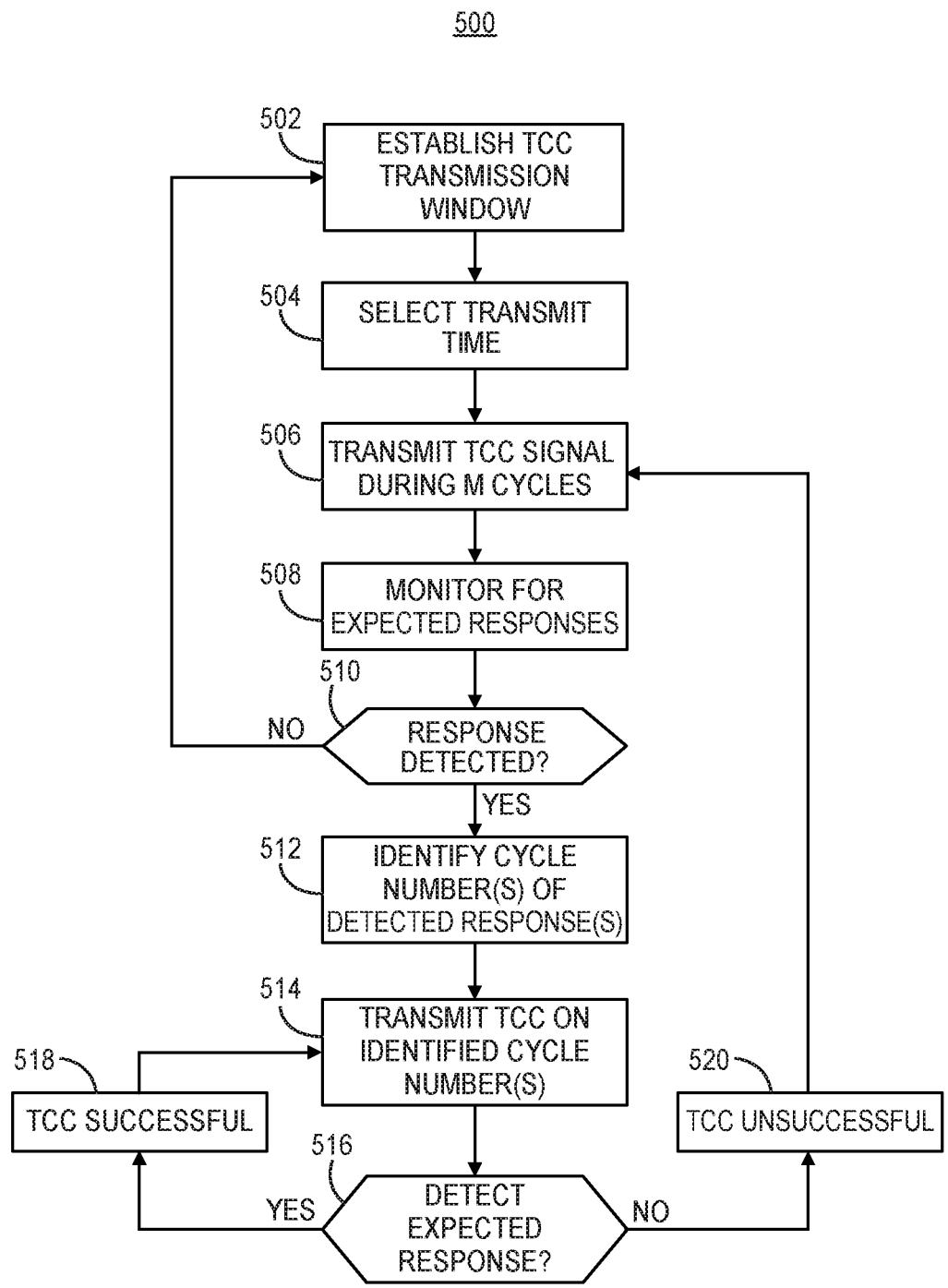
FIG. 11 is a flow chart of a method for controlling TCC in an IMD system according to another example.

FIG. 11 is a flow chart 500 of a method for controlling TCC in an IMD system according to another example. In the example of FIG. 9 described above, the transmitting device may transmit a TCC signal at a selected transmit time during every cardiac cycle. Successful TCC transmission may be confirmed based on detecting an expected response performed by the receiving device a minimum number of times N out of every M TCC signals transmitted, e.g., one response detected for every M TCC signal transmissions. In the example of FIG. 11, detection of an expected response may be used to establish on which cycles out of a series of physiological cycles, e.g., cardiac or respiratory cycles, and/or how frequently TCC signals are transmitted during a series of physiological cycles.

At block 502, the transmitting device establishes the TCC transmission window as a portion of a physiological cycle. As described above, the TCC transmission window may be defined based on a starting time established in response to detecting an expected response performed by the receiving device. The response of the receiving device may be transmission of a TCC confirmation or acknowledgement signal by the receiving device, delivery of a therapy such as a pacing pulse, transmission of requested physiological data, or transmission of a modulated TCC signal encoding TCC transmission window information, as examples. The TCC transmission window may be established by transmitting TCC signal transmissions at different times spanning across one or more cardiac cycles and/or one or more respiratory cycles. For example, during TCC testing, TCC signals may be transmitted once per cardiac cycle but at different times during each cardiac cycle to determine which time(s) result in an expected response performed by the receiving device. Other techniques for establishing the TCC transmission window are described above.

At bock 504, a transmission time within the TCC transmission window is selected by the transmitting device for transmitting a TCC signal. In the example of RA pacemaker 100 being the transmitting device and RV pacemaker 70 being the receiving device, the transmission window may be established as a portion of the cardiac cycle. The transmission time within the TCC transmission window may be the start of the transmission window or a selected time within the transmission window that facilitates timing control of a desired response performed by the receiving device, such as delivering a triggered ventricular pacing pulse at a desired AV interval.

At block 506, TCC transmitter 90 is controlled by control circuit 170 to transmit a TCC signal during the transmission window during each one of a series of M cardiac cycles. In other examples, the TCC transmission window may be established as a portion of a respiratory cycle. TCC signals may be transmitted during the transmission window during each one of a series of M respiratory cycles at block 506.

At block 508, control circuit 170 monitors for an expected response performed by the receiving device following each one of the TCC signals transmitted during the M cycles. If no expected responses are detected as determined at block 510, control circuit 170 may return to block 502 to re-establish the TCC transmission window. If at least one response is detected out of the M TCC signal transmissions, control circuit 170 identifies the cycle number out of the M cycles during which the expected response is detected (block 512). To illustrate, if a TCC signal is transmitted from RA pacemaker 100 to RV pacemaker 70 during the TCC transmission window of each one of eight consecutive cardiac cycles, the expected response may be detected by RA pacemaker 100 during only the sixth cardiac cycle of the eight cycles. In another illustrative example, the expected response may be detected on only the second and the seventh cardiac cycles of the eight cardiac cycles. The identified cycle(s) corresponding to detected responses performed by the receiving device may correspond to a relative increase in transimpedance between the transmitting electrode vector and the receiving electrode vector that occurs cyclically with the cardiac cycle and/or the respiratory cycle as shown in FIG. 6.

At block 514, the control circuit of the transmitting device controls TCC transmitter 90 to transmit TCC signals only on the identified cycle number(s) corresponding to detected response(s) performed by the receiving device. In the illustrative example given above in which a response was detected only during the sixth cycle of the series of eight cardiac cycles, TCC signals may subsequently be transmitted only on the sixth cardiac cycle of every non-overlapping series of eight cardiac cycles. If the expected response was detected on the second and seventh cardiac cycles, the TCC transmitter 90 may be controlled to transmit TCC signals only on the second and/or seventh cardiac cycles of each subsequent series of eight cardiac cycles. If the expected response is received for any two or more consecutive cycles of the M physiological cycles, the control circuit of the transmitting device may select which of the cycles for transmitting a TCC signal during each subsequent, non-overlapping series of M cycles.

As such, the control circuit of the transmitting device may select which cycles as well as how many cycles out of a series of M physiological cycles that TCC signals are transmitted based on identifying the cycle numbers of detected responses performed by the receiving device. In the example of the receiving device being RV pacemaker 70, the TCC signals may be transmitted as few as once every eight cardiac cycles for establishing an AV pacing interval and/or ventricular pacing rate. RV pacemaker 70 may pace at a fixed pacing interval until the next TCC signal is received. In the examples presented here, M is set to eight cycles, however it is recognized that the number of cycles in each successive series of physiological cycles may be less than or greater than eight.

At block 516, the transmitting device confirms detection of an expected response performed by the receiving device. If TCC signals are transmitted only once during one identified cycle out of each series of M cycles, one expected response performed by the receiving device and detected at block 516 during the M cycles is confirmation of successful TCC transmission at block 518. The control circuit of the transmitting device continues to transmit TCC signals on the identified cycle number of each series of M cycles at block 514. If TCC signals are transmitted during more than one identified cycle of the series of M cycles at block 514, detection of the expected response performed by the receiving device may be required for only one or up to all of the transmitted TCC signals in order to confirm successful TCC transmission at block 518. The required number of detected responses during a series of M cycles may be less than the number TCC signals transmitted during the M cycles if TCC signals are transmitted during more than one cycle of the M cycles.

If the required number of expected responses is not detected during the series of M cycles ("no" branch of block 516), the control circuit of the transmitting device determines that TCC is unsuccessful at block 520. The control circuit may return to block 506 to control the TCC transmitter 90 to transmit the TCC signal during the previously established transmission window during each one of the next series of M cycles. The control circuit may re-determine the cycle number(s) during the next series of M cycles for which an expected response performed by the receiving device is detected. After re-determining the cycle number(s) of the M cycles that correspond to the expected response detection(s), the control circuit of the transmitting device transmits TCC signals during only the identified cycle numbers of each non-overlapping series of M cycles at block 514. TCC signals may be transmitted during one or more of the identified cycles of the series of M cycles. If no response is detected at block 510 during the M cycles, the control circuit of the transmitting device may be required to return to block 502 to re-establish the transmission window. In this way, TCC transmission may be optimized to occur during a time window corresponding to cyclical periods of relatively increased transimpedance. Success of TCC transmission is promoted while conserving the power required for generating TCC signals by transmitting TCC signals less often than every cardiac and/or every respiratory cycle.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, an IMD system capable of TCC has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A device comprising:
   a housing;
   a tissue conduction communication (TCC) transmitter enclosed by the housing and configured to generate TCC signals for transmission via a transmitting electrode vector coupled to the TCC transmitter; and
   a control circuit enclosed by the housing and coupled to the TCC transmitter and configured to:
   control the TCC transmitter to transmit a TCC test signal at each of a plurality of time points over a transmission test period;
   detect at least one response to the transmitted TCC test signals performed by the receiving device;
   establish a transmission window based on the at least one response so that the transmission window is correlated to a time during the transmission test period of relative increased transimpedance between the transmitting electrode vector and a receiving electrode vector of the receiving device; and
   control the TCC transmitter to transmit a communication signal to the receiving device during the transmission window.

2. The device of claim 1, wherein the control circuit is further configured to:
   select a TCC signal transmission time within the transmission window based on a pacing interval; and
   transmit the TCC signal to the receiving device during the transmission window as a pacing trigger signal transmitted at the selected TCC signal transmission time.

3. The device of claim 1, wherein the control circuit is configured to detect the at least one response by detecting at least an earliest occurring acknowledgement signal transmitted from the receiving device in response to the transmitted TCC test signals.

4. The device of claim 1, wherein the control circuit is configured to detect the at least one response by receiving a TCC data signal from the receiving device, the TCC data signal comprising timing information correlated to a time of maximum transimpedance during the transmission test period.

5. The device of claim 1, wherein the control circuit is configured to detect the at least one response by detecting evidence of a therapy delivered by the receiving device.

6. The device of claim 1, further comprising a sensor configured to produce a signal correlated to a physiological condition of the patient,
   wherein the control circuit is configured to re-establish the transmission window in response to a change in the sensor signal.

7. The device of claim 6, wherein:
   the sensor comprises an accelerometer configured to produce a signal correlated to at least one of patient physical activity or patient body posture; and
   the control circuit is configured to re-establish the transmission window in response to detecting a change in at least one of patient physical activity or patient body posture based on the accelerometer signal.

8. The device of claim 1, wherein the control circuit is further configured to:
   detect failure of the transmitted TCC signal; and
   in response to a threshold number of detected failures of transmitted TCC signals being reached, re-establish the transmission window.

9. The device of claim 1, wherein the control circuit is further configured to:
   establish the transmission window as a portion of a physiological cycle;
   control the TCC transmitter to transmit a TCC signal during the transmission window during each of a predetermined number of the physiological cycles defining a first series of the physiological cycles;
   monitor for an expected response performed by the receiving device in response to each one of the TCC signals transmitted during the respective transmission windows;
   detect successful TCC transmission during the first series in response to only a single expected response being detected during the first series.

10. The device of claim 1, wherein the control circuit is further configured to:
    establish the transmission window as a portion of a physiological cycle;
    control the TCC transmitter to transmit a TCC signal during the transmission window during each one of a first series of a predetermined number of the physiological cycles;
    monitor for an expected response performed by the receiving device following each one of the TCC signals transmitted during the first series;
    identify each cycle number of the predetermined number of cycles corresponding to a detected response performed by the receiving device during the first series; and
    control the TCC transmitter to transmit a TCC signal during only cycles corresponding to the identified cycle numbers during a second series of the predetermined number of physiological cycles subsequent to the first series.

11. The device of claim 10, wherein the control circuit is further configured to:
detect an unsuccessful TCC transmission in response to not detecting the expected response performed by the receiving device during the second series;
control the TCC transmitter to transmit the TCC signal during the transmission window during each one of the predetermined number of physiological cycles during a third series of the predetermined number of the physiological cycles subsequent to the second series;
detect the expected response performed by the receiving device in response to at least one of the TCC signals transmitted during the third series;
re-identify each cycle number of the third series corresponding to the detected expected response; and
control the TCC transmitter to transmit a TCC signal only during cycles corresponding to the re-identified cycle number(s) during a fourth series of the predetermined number of physiological cycles subsequent to the third series.

12. The device of claim 1, wherein the control circuit is further configured to:
detect at least one event comprising at least one of a cardiac event or a respiratory event; and
enable the established transmission window in response to the at least one detected event for controlling the transmitting of the TCC signal during the transmission window.

13. The device of claim 1, wherein the control circuit is further configured to control the TCC transmitter to:
generate the TCC signal that is transmitted during the transmission window to have a first power;
generate a second TCC signal having a second power greater than the first power; and
transmit the second TCC signal outside the transmission window.

14. A method comprising:
transmitting a tissue conduction communication (TCC) test signal at each of a plurality of time points over a transmission test period via a transmitting electrode vector coupled to a TCC transmitter;
detecting at least one response to the transmitted TCC test signals performed by a receiving device;
establishing a transmission window based on the at least one response so that the transmission window is correlated to a time during the transmission test period of relative increased transimpedance between the transmitting electrode vector and a receiving electrode vector of the receiving device; and
transmitting a TCC signal to the receiving device during the transmission window.

15. The method of claim 14, further comprising:
selecting a TCC signal transmission time within the transmission window based on a pacing interval; and
transmitting the TCC signal during the transmission window as a pacing trigger signal transmitted at the selected TCC signal transmission time.

16. The method of claim 14, wherein detecting the at least one response comprises detecting at least an earliest occurring acknowledgement signal transmitted from the receiving device in response to the transmitted TCC test signals.

17. The method of claim 14, wherein detecting the at least one response comprises receiving a TCC data signal from the receiving device, the TCC data signal comprising timing information correlated to a time of relative increased transimpedance during the transmission test period.

18. The method of claim 14, wherein detecting the at least one response comprises detecting evidence of a therapy delivered by the receiving device.

19. The method of claim 14, further comprising:
producing by a sensor of the IMD a signal correlated to a physiological condition of the patient; and
re-establishing the transmission window in response to a change in the sensor signal.

20. The method of claim 19, further comprising:
producing the sensor signal by producing an accelerometer signal correlated to at least one of patient physical activity or patient body posture; and
re-establishing the transmission window in response to detecting a change in at least one of patient physical activity or patient body posture based on the accelerometer signal.

21. The method of claim 14, wherein the control circuit is further configured to:
detect failure of the transmitted TCC signal; and
in response to a threshold number of detected failures of transmitted TCC signals being reached, re-establish the transmission window.

22. The method of claim 14, further comprising:
establishing the transmission window as a portion of a physiological cycle;
transmitting a TCC signal during the transmission window during each of a predetermined number of the physiological cycles defining a first series of the physiological cycles;
monitor for an expected response performed by the receiving device in response to each one of the TCC signals transmitted during the respective transmission windows;
detect successful TCC transmission during the first series in response to only a single expected response being detected during the first series.

23. The method of claim 14, further comprising:
establishing the transmission window as a portion of a physiological cycle;
transmitting a TCC signal during the transmission window during each one of a first series of a predetermined number of the physiological cycles;
monitoring for an expected response performed by the receiving device following each one of the TCC signals transmitted during the first series;
identifying each cycle number of the predetermined number of cycles corresponding to a detected response performed by the receiving device during the first series; and
controlling the TCC transmitter to transmit a TCC signal during only cycles corresponding to the identified cycle numbers during a second series of the predetermined number of physiological cycles subsequent to the first series.

24. The method of claim 23, further comprising:
detecting an unsuccessful TCC transmission in response to not detecting the expected response performed by the receiving device during the second series;
transmitting the TCC signal during the transmission window during each one of the predetermined number of physiological cycles during a third series of the predetermined number of the physiological cycles subsequent to the second series;

detecting the expected response performed by the receiving device in response to at least one of the TCC signals transmitted during the third series;

re-identifying each cycle number of the third series corresponding to the detected expected response; and transmitting a TCC signal only during cycles corresponding to the re-identified cycle number(s) during a fourth series of the predetermined number of physiological cycles subsequent to the third series.

25. The method of claim 14, further comprising:

detecting at least one event comprising at least one of a cardiac event or a respiratory event; and enable the established transmission window in response to the at least one detected event for controlling the transmitting of the TCC signal during the transmission window.

26. The method of claim 14, further comprising:

generating the TCC signal that is transmitted during the transmission window to have a first power;

generating a second TCC signal having a second power greater than the first power; and transmitting the second TCC signal outside the transmission window.

27. A non-transitory, computer-readable storage medium comprising a set of instructions which, when executed by device, cause the device to:

transmit a tissue conduction communication (TCC) test signal at each of a plurality of time points over a transmission test period to a receiving device via a transmitting electrode vector coupled to a TCC transmitter and a conductive tissue pathway in a patient;

detect at least one response to the transmitted TCC test signals performed by the receiving device;

establish a transmission window based on the at least one response so that the transmission window is correlated to a time during the transmission test period of relative increased transimpedance between the transmitting electrode vector and a receiving electrode vector of the receiving device; and transmit a TCC signal to the receiving device during the transmission window.

* * * * *